United States Patent

Hallinan et al.

[11] Patent Number: 6,103,934
[45] Date of Patent: Aug. 15, 2000

[54] MANUFACTURING AND PROCESS CONTROL METHODS

[75] Inventors: Noel Hallinan; James A. Hinnenkamp, both of Cincinnati, Ohio

[73] Assignee: Millennium Petrochemicals, Inc., Cincinnati, Ohio

[21] Appl. No.: 09/216,330

[22] Filed: Dec. 18, 1998

[51] Int. Cl.[7] .............................. C07C 51/10; C07C 51/12
[52] U.S. Cl. ............................................ 562/517; 562/519
[58] Field of Search ...................................... 562/517, 519

[56] References Cited

U.S. PATENT DOCUMENTS

| | | |
|---|---|---|
| 4,000,170 | 12/1976 | Forster et al. . |
| 4,627,008 | 12/1986 | Rosenthal . |
| 5,121,337 | 6/1992 | Brown . |
| 5,317,379 | 5/1994 | Ryan et al. . |
| 5,468,961 | 11/1995 | Gradon et al. . |
| 5,596,992 | 1/1997 | Haaland et al. . |
| 5,604,132 | 2/1997 | Capuano et al. . |
| 5,691,701 | 11/1997 | Wohlstein et al. . |
| 5,817,869 | 10/1998 | Hinnenkamp et al. . |

OTHER PUBLICATIONS

J.A. Dean: "Analytical Chemistry Handbook." McGraw Hill, Inc., (1995).

*Primary Examiner*—Ardin H. Marschel
*Assistant Examiner*—Sherif Kafafi
*Attorney, Agent, or Firm*—Wood, Herron & Evans, L.L.P.

[57] ABSTRACT

There is provided a process control method for the production of acetic acid by the catalyzed carbonylation of methanol and a process for the manufacture of acetic acid using the process control method. The process control method comprises measuring various reactor component concentrations, specifically the active catalyst species, methyl iodide, water and methyl acetate by means of an infrared analyzer, and adjusting in response thereto the concentrations of at least the catalyst species, methyl iodide and water to optimize the acetic acid reaction.

43 Claims, 14 Drawing Sheets

MANUFACTURING AND PROCESS CONTROL METHODS

FIELD OF THE INVENTION

This invention relates to a method of improving process control in the manufacture of acetic acid, and a method of manufacturing acetic acid utilizing improved process control.

BACKGROUND OF THE INVENTION

In some chemical processes, it is necessary to monitor the progress of the chemical reaction and to adjust the supply of the reactants to ensure that the reaction proceeds as desired. The production of acetic acid, which is an important commercial commodity, is one such chemical process. One current method of manufacturing acetic acid, by carbonylation of methanol or its derivatives, such as methyl acetate or methyl iodide, involves a chemical reaction initiated by a Group 9 catalyst system, specifically as an iridium or rhodium coordination compound in the presence of an iodide and water. Carbonylation has become a preferred route to make acetic acid. Nevertheless, there are countervailing considerations which affect implementation of this process. First, the underlying reaction chemistry is intricate, involving a number of interrelated reactions, by-products and equilibria, all of which must be properly balanced, one against the other, to make the process practicable and maximize efficiency of raw material utilization. Also, the catalyst systems, such as coordination compounds of rhodium, iridium and the like, required for carbonylation are generally complex and expensive. Moreover, carbonylation catalyst systems are extraordinarily sensitive to changes in any number of reaction parameters which, in turn, adversely affect catalyst stability and activity.

It is known to manually sample the reactor effluent and perform a separate laboratory analysis of component concentrations using multiple instrumental and wet chemical methods. This procedure is labor intensive and time consuming, resulting in long time lapses between sampling and the characterization of the sample. This method of sample characterization realistically permits generation of a limited number of data points per day, typically about 3 to about 8. Also, because of the delay between sampling and generation of data, the sample characterization would provide an evaluation of a reactor system which may lag behind the actual status of the system by several hours.

Infrared analysis has been used for characterizing components of a chemical process stream. Infrared spectroscopy permits both qualitative and quantitative analyses. Sample analyses can be performed on both organic and inorganic species. Because nearly every molecule has an infrared spectrum, infrared spectroscopy is generally capable of characterizing every molecular component of a chemical process stream without destroying or otherwise modifying the components.

In monitoring the manufacture of acetic acid, the infrared energy absorption corresponding to the stretching frequencies of the hydroxyl and carbonyl groups of acetic acid generates broad absorption bands which tend to overlap, and therefore mask, the infrared bands indicating the presence of a rhodium or iridium catalyst.

In an effort to characterize, for example, rhodium in a rhodium-catalyzed carbonylation system, other methods of analysis have been employed, such as atomic absorption and inductively coupled plasma analysis. However, it is difficult to obtain rhodium concentration data of acceptable precision by either atomic absorption or inductively coupled plasma analysis. Both of these methods involve working up the sample to form a liquid matrix. The process of working up the sample also increases the risk of introducing air into the sample and thereby causing rhodium precipitation. Because of the unreliability of such analyses, the addition of rhodium to the reaction system has been based on an empirical relationship based on carbon dioxide production. However, this empirical relationship is subject to error when other operating conditions are changed, particularly at high operating rates.

It is highly desirable to be able to produce acetic acid under reduced water process conditions without sacrificing catalyst productivity and stability.

Normally, the carbonylation process proceeds at a water level of about 11–14% by weight to maintain the catalyst in its active form. However, that quantity of water must later be separated from the acetic acid produced in the process, increasing processing time and cost. In U.S. Pat. No. 5,817,869 incorporated herein by reference in its entirety, the carbonylation system was modified to achieve low water carbonylation by adding a pentavalent Group 15, formerly Group VA, oxide. Group 15 includes the elements N, P, As, Sb and Bi. Although this new system successfully achieves high yields and reaction rates while stabilizing the active rhodium catalyst component, this modification to achieve low water processing increases the need for a reliable technique to determine the soluble rhodium content.

It is thus desirable to provide a reactant monitoring system that allows for more frequent monitoring of the chemical reaction in the production of acetic acid, particularly where low water processing techniques are utilized. In addition, because of the complexity of the catalyzed carbonylation reaction, monitoring of the catalyst concentration to the exclusion of other reactants is less likely to provide an accurate assessment of the status of the reaction system. It is thus also desirable to be able to monitor and adjust the concentration of up to all of the reactants of the system including the catalyst species based on direct analysis of the reactants. Further, it is desirable to utilize a reactant monitoring system to improve the efficiency of manufacturing acetic acid.

SUMMARY

The present invention is directed to a process for monitoring and controlling the concentration of reactor components in the production of acetic acid by the catalyzed carbonylation of methanol that measures the concentration values of at least the active catalyst species, methyl iodide, water and methyl acetate reaction components, with adjustment of at least methyl iodide, water and the active catalyst species to optimize the reaction. The invention is also directed to the process of manufacturing acetic acid based on the process control procedure described herein.

In a preferred embodiment of the present invention, acetic acid is produced by a low water carbonylation reaction incorporating a Group 15 oxide in the reaction solution, and the invention encompasses monitoring and adjusting the concentration of the Group 15 oxide. Preferably, monitoring is performed near in time to removal of sample from the reactor, and most preferably is conducted online. As described herein, online measurement refers to the analysis of a process solution in real time or substantially real time either by direct insertion of a probe into the process vessel of interest or by rapidly circulating process solution through an analyzer and subsequently returning this solution to the process. Off-line measurement refers to the irreversible removal of a sample from a process and subsequent analysis being performed on laboratory instrumentation. Further, it is preferred that adjustment of component concentrations and reaction parameters as required be performed substantially immediately following characterization of the sample. Preferably, this adjustment is performed automatically in response to the sample characterization. Finally, it is preferred that the sampling be performed often to minimize undesirable drift from optimum reaction efficiency.

These and other objects and advantages of the present invention shall become more apparent from the accompanying drawings and description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the principles of the invention.

DETAILED DESCRIPTION

The method in its broader aspects is practiced by collecting a sample of an acetic acid reaction mixture containing at least methyl iodide, water, methyl acetate and an active catalyst species of a catalyst selected from the group consisting of rhodium and iridium; measuring the concentration of methyl iodide, water, methyl acetate and the active catalyst species in an infrared analyzer; and adjusting the concentration of at least methyl iodide, water, and the active catalyst species in the acetic acid reaction mixture in response to the measured concentrations of methyl iodide, water, methyl acetate and active catalyst species. The process of manufacturing acetic acid based on improved process control of at least these reaction components is also described.

Preferably the infrared analyzer is a Fourier Transform infrared spectrometer. Analysis of reaction components is conducted in the infrared cells which operate in one or more of the mid-infrared regions and the extended mid-infrared region. Preferably, the adjustment of concentrations of at least methyl iodide, water and the active catalyst species in the acetic acid reaction mixture produces a substantially constant concentration for each of the methyl iodide, water, methyl acetate and active catalyst species during the manufacture of acetic acid.

The process control is facilitated by frequent measurement of the reactant components in the acetic acid reactor. The frequency of measurement should be effective to maintain a substantially constant concentration of at least methyl iodide, water, methyl acetate and active catalyst species during the manufacture of acetic acid. It has been found that a measurement frequency of approximately thirty times per hour produces good results.

The active catalyst species may be the active species of either an iridium or rhodium catalyst. In the examples provided herein, the active species utilized was of a rhodium catalyst.

Figure 1:
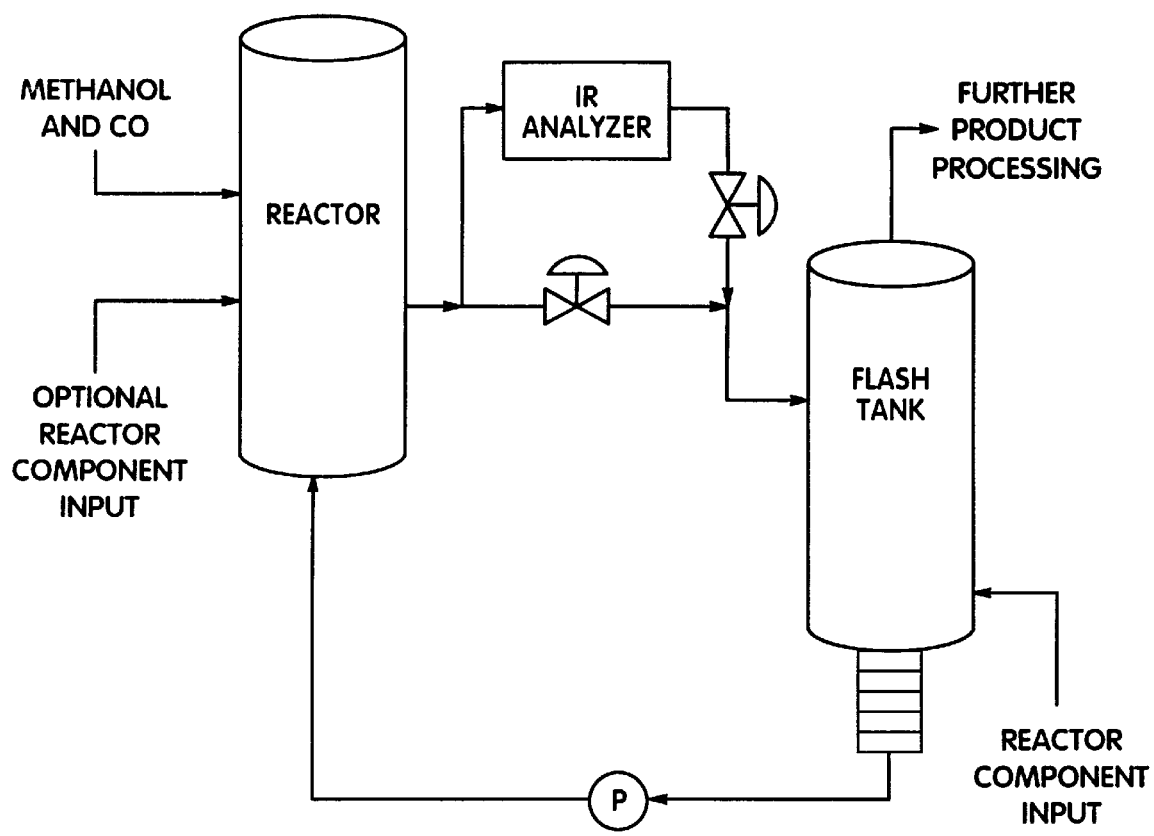
FIG. 1 is a schematic representation of one mode of the online analysis of the present invention.

FIG. 1 is a schematic representation of one mode of the present invention for monitoring online the carbonylation of methanol to acetic acid, and adjusting reactor components as necessary. To monitor the components of the reaction system for the production of acetic acid, a sample or slipstream is collected from the reactor effluent and transferred through an infrared analyzer to a low pressure flash tank. The sample is then analyzed, as will be discussed in detail hereafter, and the results fed to a display or control unit. The concentrations of one or more reactor components are adjusted in response thereto so as to optimize reaction efficiency. These reactor components mainly include water, methyl iodide (MeI), and rhodium catalyst ($Rh(CO)_2I_2^-$). Addition of one or more reactor components to the reactor is typically effected through the flash tank, though direct injection into the reactor is an option. Acetic acid produced in the reactor is withdrawn for purification or other processing through the flash tank. The pure acetic acid product is removed from the system, and most of the remaining components are recycled to the reactor. A small amount of byproducts are removed from the system and disposed of. Methyl acetate (MeOAc) levels in the system are generally adjusted indirectly by adjusting one or more of methyl iodide, active rhodium species or water concentration, and the reaction temperature. Alternatively, methyl acetate can be added directly to the reaction system.

The reaction system may optionally contain a pentavalent Group 15 oxide of the formula $R_3M=O$ to generate acetic acid via a low water process, as disclosed in U.S. Pat. No. 5,817,869 entitled "Use of Pentavalent Group VA Oxides in Acetic Acid Processing", incorporated herein by reference in its entirety. In the formula $R_3M=O$, M is an element from Group 15 of the periodic table and each R is independently a substituted or unsubstituted alkyl, aryl, aralkyl or alkaryl group. Because the Group 15 element (formerly Group VA) is preferably phosphorus, as disclosed in that application, the pentavalent Group 15 oxide will hereafter be referred to as phosphine oxide or triphenyl phosphine oxide, though other oxides disclosed in U.S. Pat. No. 5,817,869 may be used. Phosphine oxide concentration may be analyzed and adjusted according to the principles of the present invention.

In the manufacture of acetic acid by carbonylation of methanol, the use of a transition metal catalyst, such as rhodium or iridium, will allow the reaction to proceed at greatly reduced pressures and temperatures compared to the uncatalyzed reaction. For ease of the discussion herein, a rhodium-catalyzed carbonylation system will be described. It is to be understood, however, that iridium-catalyzed systems are contemplated to be within the scope of the present invention. In the rhodium-catalyzed carbonylation system, methanol and carbon monoxide are brought into contact in a reactor in the presence of water, methyl iodide, acetic acid and a homogeneous rhodium catalyst. Rapid esterification of methanol with acetic acid leads to formation of methyl acetate and water and thus only trace amounts of methanol are detected in the reactor solution. The equilibrium reaction between hydrogen iodide and methyl acetate allows a steady state concentration of methyl iodide to be maintained in order to promote the reaction.

The homogeneous rhodium catalyst may be added to the system by means of a number of rhodium-containing components, which include, without limitation: $RhCl_3$; $RhBr_3$; $RhI_3$; $RhCl_3.3H_2O$; $RhBr_3.3H_2O$; $RhI_3.3H_2O$; $Rh_2(CO)_4Cl_2$; $Rh_2(CO)_4Br_2$; $Rh_2(CO)_4I_2$; $Rh_2(CO)_8$; $Rh(CH_3CO_2)_2$; $Rh(CH_3CO_2)_3$; $Rh[(C_6H_5)_3P]_2(CO)I$; $Rh[(C_6H_5)P]_2(CO)Cl$; Rh metal; $Rh(NO_3)_3$; $Rh(SnCl_3)[(C_6H_5)_3P]_2$; $RhCl(CO)[(C_6H_5)_3As]_2$; $RhI(CO)[(C_6H_5)_3Sb]_2$; $[Y][Rh(CO)_2X_2]$, wherein X is $Cl^-Br^-$ or $I^-$; and Y is a cation selected from the group consisting of positive ions from Group 1 of the Periodic Table of Elements, such as H, Li, Na and K, or Y is a quaternary ion of N, As or P; $Rh[(C_6H_5)_3P]_2(CO)Br$; $Rh[n-C_4H_9)_3P]_2(CO)Br$; $Rh[(n-C_4H_9)_3P]_2(CO)I$; $RhBr[(C_6H_5)_3P]_3$; $RhI[(C_6H_5)_3P]_3$; $RhCl[(C_6H_5)_3P]_3$; $RhCl[(C_6H_5)_3P]_3H_2$; $[(C_6H_5)_3P]_3Rh(CO)H$; $Rh_2O_3$; $[Rh(C_3H_4)_2Cl]_2$; $K_4Rh_2Cl_2(SnCl_2)_4$; $K_4Rh_2Br_2(SnBr_3)_4$; $[H][Rh(CO)_2I_2]$; $K_4Rh_2I_2(SnI_2)_4$ and the like. Preferably the rhodium species used herein is water or acetic acid soluble. Preferred compounds are $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, or $[H][Rh(CO)_2I_2]$ with $[H][Rh(CO)_2I_2]$, $Rh(CH_3CO_2)_2$ and $Rh(CH_3CO_2)_3$ being most preferred.

Under typical reactor conditions of temperature and pressure, the reaction chemistry is quite complex and several dependent chemical equilibria contribute to reaction rate, catalyst stability and reaction selectivity. The rhodium catalyst is preferentially present as the following coordination compound, $Rh(CO)_2I_2^-$, or $Rh^I$ as used herein. Oxidative addition of methyl iodide to $Rh^I$ leads to formation of transient acetyl iodide, $CH_3COI$, which is rapidly hydrolyzed by water to form acetic acid and hydrogen iodide.

Though acetic acid will be formed via this reaction, the rate of acid formation is diminished by the presence of several competing side reactions which remove key reactants from the reaction cycle. The most prominent of these side reactions is the water gas shift reaction in which rhodium catalyzes the formation of carbon dioxide and hydrogen from carbon monoxide and water. The consequences of this side reaction include increased carbon monoxide usage and the necessity for an increased reactor purge rate in order to remove excess carbon dioxide and to maintain a set partial pressure of carbon monoxide.

Under reaction conditions, rhodium will be present as a mixture of the active form $Rh^I$ and the inactive form, $Rh(CO)_2I_4^-$, or $Rh^{III}$ as used herein. The latter species is an intermediate in the water gas shift cycle. The presence of a steady state concentration of this $Rh^{III}$ species not only adversely affects the rate of acetic formation, but also leads to decreased catalyst stability as $Rh^{III}$ species are more prone to precipitation than $Rh^I$ species. Thus, maximizing rhodium as $Rh^I$ is a key step in improving methanol carbonylation technology.

Reactor conditions for the present invention encompass temperatures of about 170° C. to about 200° C. and a pressure of about 350 psig to about 450 psig. At higher temperatures, the reactor equipment components typically made from Hastelloy™ B2 are subject to unacceptable corrosion risk. At lower temperatures, the reaction rate is unacceptably slow.

In one embodiment, the temperature of the collected sample is controlled within a range so as to optimally both quench the reaction in the sample and prevent precipitation of any solids. If the temperature is too high, the carbon monoxide content becomes depleted through continued reaction in the sample. If the temperature is too low, one or more of $Rh^{III}$ and the optional phosphine oxide promoter could precipitate out. This precipitation will not only alter the measured concentration, but will also tend to cause blockages in the transfer lines.

One method of monitoring the reactor solution in situ is by using an attenuated total reflectance (ATR) probe with a suitable crystal material. Transfer of light signal to the detector can be achieved by light pipe, chalcogenide fiber or other methods known to those skilled in the art of infrared spectroscopy. Using a similar analysis technique, this probe could optionally be inserted into the reactor or a reactor slipstream to provide online analysis capability. Alternately, a reactor slipstream is passed through an infrared analyzer equipped with either a flow through ATR cell or flow through transmission cell. Preferably, continuous flow is employed and reactor solution is subsequently returned to the reaction system via the (low pressure) flash tank. By using a back pressure regulator or similar device located after solution has passed through the cells, essentially no pressure drop occurs across the cells. This ensures that analysis is performed with minimal change from the reactor pressure thereby resulting in no degassing or bubble formation in the cells. These latter effects, if present, would severely impact solution component quantitation. The temperature of the slipstream can be maintained anywhere between ambient and process temperature. Thus, a temperature range of 20° C.–200° C. is contemplated. Optimal temperature is governed by several parameters, such as precipitation of solids, compatibility of cell window or crystal materials with process conditions, and controlling process reaction in the slipstream. The most preferred temperature range of the slipstream is 30° C.–120° C. It is generally undesirable to operate at or below 30° C. as select reactor components show increasing propensity to precipitate as temperature is lowered. It is also preferred to operate at or below 120° C. in order that reaction substantially quenches in the transfer lines, thus ensuring that the measured analyte concentrations are representative of the concentrations in the reactor immediately prior to sampling. Finally, optimal operating temperature is a function of the particular cell window material used.

Another alternative process control technique is laboratory off-line analysis of a reactor sample by FTIR. While not as desirable as the most preferred embodiment of real time measurement as provided by online analysis, laboratory FTIR does provide significant advantages over conventional off-line methods of analysis. In particular, all components can be measured simultaneously by one mid-infrared measurement. The conventional alternative analysis involves using gas chromatography, Karl Fischer, hygrometer, titrimetric methods and ICP or AA. In addition, ICP/AA requires extensive sample pretreatment prior to analysis. Thus, in terms of feedback for process control, reactor component concentrations as determined by FTIR can be available in as little as 7 minutes after sample receipt in the lab, compared to a minimum of 1 hour in the case of the non-FTIR methods. The sample can be analyzed at ambient pressure and temperature using either the probe or transmission cell technology described above.

Depending on the temperature employed, the cell window or crystal material can be selected from the group of materials including $CaF_2$, ZnS, sapphire, AMTIR (Se-Ge-As composite), Ge, ZnSe, Si, diamond, KRS-5 (thallium bromoiodide), or cubic zirconia. The nature of these materials in terms of composition, transmission ranges, and the like are well known to those skilled in the art of spectroscopy and are readily available in spectroscopic and vendor literature. In a preferred embodiment of this invention, involving transmission cell analysis of a slipstream, sapphire windows are used. Sapphire has the appropriate transmission range to allow the analysis to be performed. It also displays good mechanical strength, chemical resistance and resistance to etching in the process described hereinabove.

In the process of monitoring the status of the reaction, the sample to be analyzed is transferred from the reactor to the analyzer and ultimately to a flash tank, with the pressure decreasing from approximately 400 psig to about 20–30 psig in the flash tank. As described hereinabove, the bulk of the pressure drop occurs only after the reactor solution has passed through the cells. Generally, the differential pressure controls the movement of reactor solution from the reactor to the infrared analyzer and the flash tank. A differential of only about 10–15 psig is sufficient to transfer the sample from the reactor. A circulation pump may also be utilized to move the fluid through the transfer line, thus eliminating the need to decrease the pressure of the system. Alternatively, the sample material may be analyzed as a side stream from the reactor unit. This sample would be analyzed under the same conditions of temperature and pressure as the reactant material, and therefore, would not be susceptible to precipitation. However, the temperature would result in continued reaction, requiring that sample analysis be conducted promptly. All tubing, valving and the like contacting the reaction solution must be chemically inert to the reaction components and be capable of withstanding corrosive attack under reaction conditions. A representative manufacturing material is Hastelloy™ B2, a Ni—Mo—Fe alloy. Other suitable materials include Hastelloy™ B3 (also a Ni—Mo—Fe alloy) and zirconium.

A number of options are available as to how the monitoring of the acetic acid reaction components may be performed.

Monitoring can be carried out by analyzing in a combination of select spectral ranges of traditional mid (400–4000 $cm^{-1}$) and extended mid-(4000–7000 $cm^{-1}$) infrared regions. One option involves a dual transmission cell, dual detector setup in which reactor solution sequentially flows through both cells. These cells differ only in pathlength. One cell has a pathlength of 0.05–0.15 mm which allows for analysis in the spectral region between 1800–5600 $cm^{-1}$ and thereby encompasses portions of traditional mid- and extended mid-infrared regions. The second cell has a pathlength of 0.2–3.0 mm which allows for analysis only in the extended mid-infrared region. The different cell pathlengths are utilized to both counteract the highly absorbing nature of acetic acid and take advantage of the two different spectroscopic regions for reactant component characterization.

Optionally, monitoring of the reaction components can be carried out using a single transmission cell, single detector setup. Depending on the cell pathlength chosen, different spectral regions can be used. A cell of pathlength 0.05–0.15 mm as described above allows quantitation of all components absorbing in the spectral region between 1800–5600 $cm^{-1}$. This region is commonly referred to as the non fingerprint region and encompasses portion of both the traditional mid-infrared region and extended mid-infrared region as noted above. Alternately, a cell of much shorter pathlength, 0.005–0.015 mm allows access to both the non fingerprint region (1800–5600 $cm^{-1}$) and the fingerprint region, which is 1800–400 $cm^{-1}$. This shorter pathlength can also be effectively achieved by using an attenuated total reflectance (ATR) crystal rather than a transmission cell. As is known to those skilled in the art, utilization of a single cell or ATR crystal in analysis of the acetic acid reaction mixture involves accepting a compromise between the extent of the range of infrared spectrum analyzed and the quantitative accuracies of concentration of certain components in the mixture. Measurement accuracies and precisions differ for different reaction components in different spectral regions using different cell pathlengths. Thus, the accuracy and precision required for a particular analysis dictates the choice of type of cell or cells, pathlength and transmission range.

The following table, Table 1, shows the spectral regions where the nine solution chemical compounds described herein and constituting the primary components of the rhodium-catalyzed acetic acid reaction can be quantified.

TABLE 1

| Component | Extended Mid (4000–7000 cm$^{-1}$) | Non Finger-Print Mid (1800–4000 cm$^{-1}$) | Fingerprint Mid (400–1800 cm$^{-1}$) |
|---|---|---|---|
| Rh$^I$ | No | Yes | No |
| Rh$^{III}$ | No | Yes | No |
| CO$_2$ (Soln.) | No | Yes | No |
| Methyl Acetate | Yes | Yes | Yes |
| Methyl Iodide | Yes | Yes | Yes |
| RI, where R = H, Group 1, 6, 7, 9, 11, 12 Metals and I = iodide | Yes | Yes | Yes |
| Triphenyl Phosphine Oxide | Yes | Yes | Yes |
| H$_2$O | Yes | Yes | Yes |
| Acetic Acid | No | No | Yes |

The flow rate to the analyzer is adjusted to optimize precision and accuracy of measurement and typically is about 10 to about 100 sccm.

Process control of the reaction for manufacturing acetic acid based on the information obtained in the analysis can be either manual or automatic. Preferably, the data obtained from the infrared analyzer is fed to a computerized control unit, which automatically adjusts the reactor components, specifically, rhodium, water, methyl iodide and triphenyl phosphine oxide, to achieve steady values for certain components. Alternatively, the data is fed to a display unit and is interpreted by an operator who adjusts reactor component concentrations manually.

The direct analysis of this type of sample from the reactor traditionally has been complicated by the sample composition, which includes both gas and liquid components. Another obstacle in obtaining accurate measurements relates to the presence of acetic acid in the system. Broadness of absorption peaks are pathlength dependent. Acetic acid exhibits carbonyl absorption in the 1400–1800 cm$^{-1}$ range of the infrared spectrum. With broadening, this absorption range overlaps with the absorption range of rhodium, which is at 1900–2100 cm$^{-1}$. Traditionally, this overlap has prevented the accurate quantitative analysis of rhodium.

In the present invention, the analysis of rhodium concentration, specifically the active rhodium species Rh(CO)$_2$I$_2^-$, i.e. Rh$^I$, is carried out in the mid-infrared region, which is from 4000 cm$^{-1}$ to 400 cm$^{-1}$. In addition to measuring the active species of rhodium, the infrared analyzer may also measure the inactive rhodium species Rh(CO)$_2$I$_4^-$, i.e. Rh$^{III}$, and Rh(CO)I$_4^-$, i.e. Rh$^{III}$ mono as used herein, and a total rhodium concentration may be obtained from the sum of the active and inactive species. Similarly, the infrared analyzer may also measure the concentration of methyl iodide and of iodide ions (I$^-$) in the reactor solution, and a total iodide concentration may be obtained from the sum of I$^-$ and methyl iodide. The analysis of methyl iodide and water takes place preferably in the extended mid-infrared region, although the analysis may also take place in the mid-infrared region.

The component that is most troublesome to analyze is methyl acetate, as its spectroscopic signature is very similar to that of the bulk acetic acid solvent. While quantitation can be carried out in either the extended mid or non fingerprint mid regions, the most effective analysis that can currently be achieved is in the fingerprint region using either an ATR cell or a transmission cell of extremely short pathlength (0.005–0.015 mm).

One advantage of the inventive process is the ability to rapidly determine the concentrations of rhodium, methyl iodide and water to generate more reliable information on the status of the reaction and thereby avoid conditions of excessively high catalyst usage. The instant invention is capable of measuring component concentrations essentially in real time, and also allows for more frequent sampling. By providing information which allows manual or automatic adjustment of concentration and other process parameters, the inventive process can improve rhodium catalyst efficiency and utilization of the reactants thereby decreasing the cost of manufacturing acetic acid while maintaining product quality.

A corollary advantage of the process control method is the ability to confirm the information provided from the rhodium catalyst measurement by the concentration measurement of the other reactants. Monitoring the concentration of other reactants present in larger quantity in the reactor permits a cross-check of the reaction conditions and a more detailed understanding of the reaction status.

In practicing the invention, measurement of rhodium, methyl iodide, water and other reactor components can be made as often as every one to two minutes, allowing the process control to very closely track the actual operating conditions within the reactor. This is a substantial improvement over the procedure of making the same measurements off-line.

In the low water carbonylation of methanol to acetic acid, the reactor effluent will also include a significant amount of phosphine oxide. The concentration of phosphine oxide is also capable of being measured and adjusted by the process control method of the present invention. The phosphine oxide promoter can be analyzed in the infrared ranges as specified in Table 1 above.

It is important that the monitoring process accurately reflect the composition of the reaction solution. Several examples of the testing of various chemometric calibration models developed on either laboratory or online infrared instrumentation are laid out below.

Figure 2A:
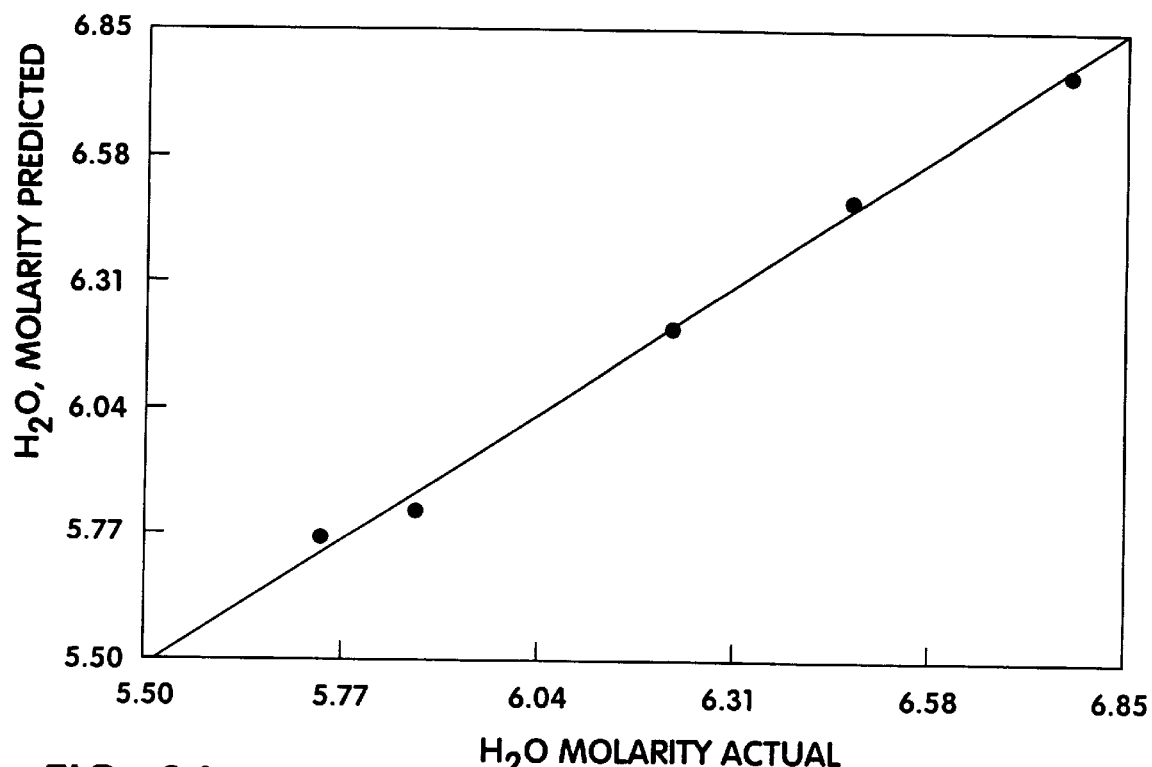
FIG. 2A is a correlation plot of actual vs. predicted concentration values showing the validation of the laboratory mid-infrared calibration model for water.
Figure 2B:
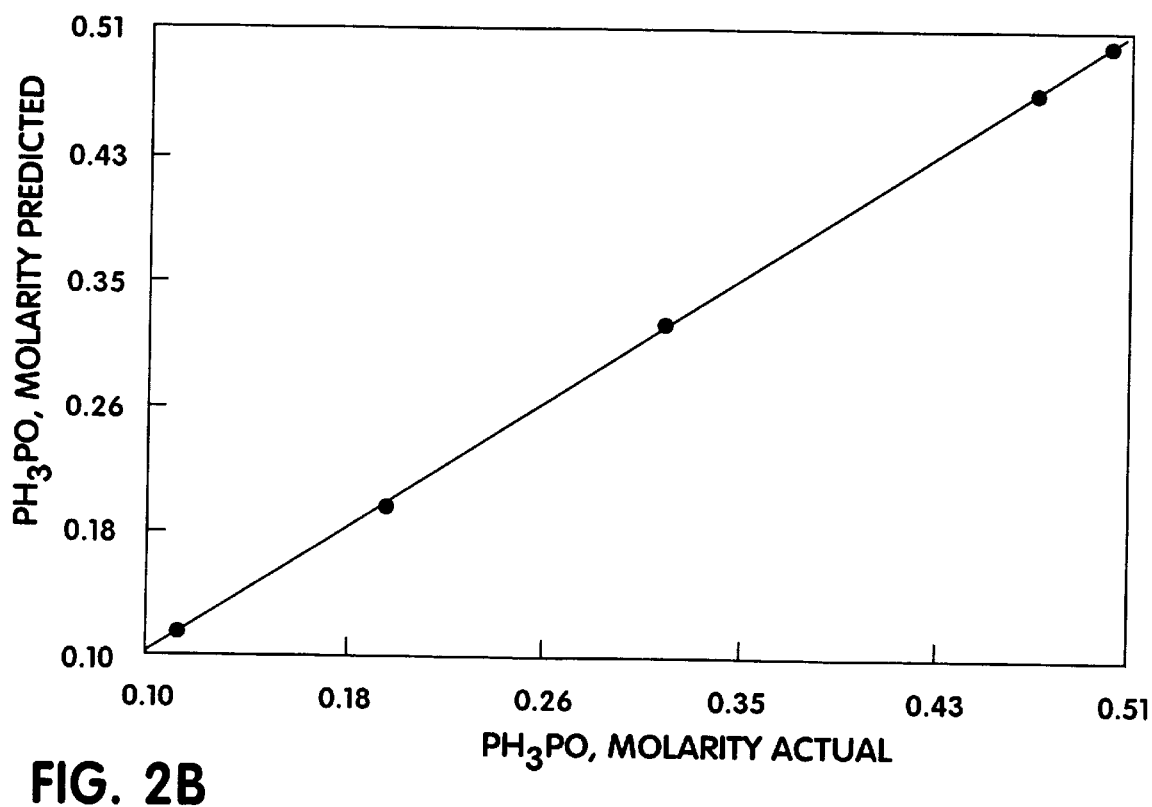
FIG. 2B is a correlation plot of actual vs. predicted concentration values showing the validation of the laboratory mid-infrared calibration model for triphenyl phosphine oxide ($Ph_3PO$)

To validate each of the chemometric calibration models developed on laboratory FTIR, five solutions were prepared, each containing known, differing amounts of phosphine oxide, water, methyl acetate, methyl iodide, hydrogen iodide and acetic acid, and each having a known measured density. These solutions were then analyzed quantitatively for molar concentration and density, with three measurements being recorded for each sample. The results tabulated below in Table 2 show close agreement between actual and predicted values for all components and also show good agreement between each of the three measurements performed for each component in each solution. For illustration purposes, this data is also represented in graphical format for water and triphenyl phosphine oxide in FIGS. 2A and 2B, respectively.

TABLE 2

Accuracy and Precision of Laboratory Mid-infrared Calibration Models
Five Prepared Samples of Known Composition Were Used

| Sample # | Ph₃PO (Molarity) | | H₂O (Molarity) | | MeI (Molarity) | | I (Molarity) | | MeOAc (Molarity) | | Density (g/ml) | |
|---|---|---|---|---|---|---|---|---|---|---|---|---|
| | Actual | Predicted | Actual | Predicted | Actual | Predicted | Actual | Predicted | Actual | Predicted | Actual | Predicted |
| 1 | 0.47 | 0.468 | 6.47 | 6.49 | 0.61 | 0.64 | 0.029 | 0.043 | 0.101 | 0.092 | 1.104 | 1.104 |
| | | 0.466 | | 6.49 | | 0.637 | | 0.039 | | 0.095 | | 1.104 |
| | | 0.467 | | 6.48 | | 0.631 | | 0.042 | | 0.091 | | 1.102 |
| 2 | 0.112 | 0.118 | 6.77 | 6.73 | 0.677 | 0.68 | 0.322 | 0.34 | 0.251 | 0.24 | 1.127 | 1.125 |
| | | 0.117 | | 6.79 | | 0.689 | | 0.32 | | 0.246 | | 1.123 |
| | | 0.116 | | 6.78 | | 0.67 | | 0.31 | | 0.243 | | 1.122 |
| 3 | 0.315 | 0.316 | 5.74 | 5.75 | 0.771 | 0.761 | 0.205 | 0.224 | 0.403 | 0.399 | 1.13 | 1.128 |
| | | 0.315 | | 5.75 | | 0.764 | | 0.216 | | 0.41 | | 1.129 |
| | | 0.32 | | 5.8 | | 0.751 | | 0.183 | | 0.407 | | 1.127 |
| 4 | 0.198 | 0.198 | 6.22 | 6.21 | 0.846 | 0.841 | 0.418 | 0.428 | 0.606 | 0.616 | 1.153 | 1.151 |
| | | 0.196 | | 6.17 | | 0.847 | | 0.397 | | 0.598 | | 1.149 |
| | | 0.197 | | 6.25 | | 0.835 | | 0.441 | | 0.599 | | 1.15 |
| 5 | 0.502 | 0.499 | 5.87 | 5.93 | 0.844 | 0.821 | 0.15 | 0.146 | 0.899 | 0.921 | 1.353 | 1.135 |
| | | 0.498 | | 5.82 | | 0.823 | | 0.153 | | 0.91 | | 1.134 |
| | | 0.497 | | 5.82 | | 0.832 | | 0.132 | | 0.916 | | 1.134 |

Figure 3:
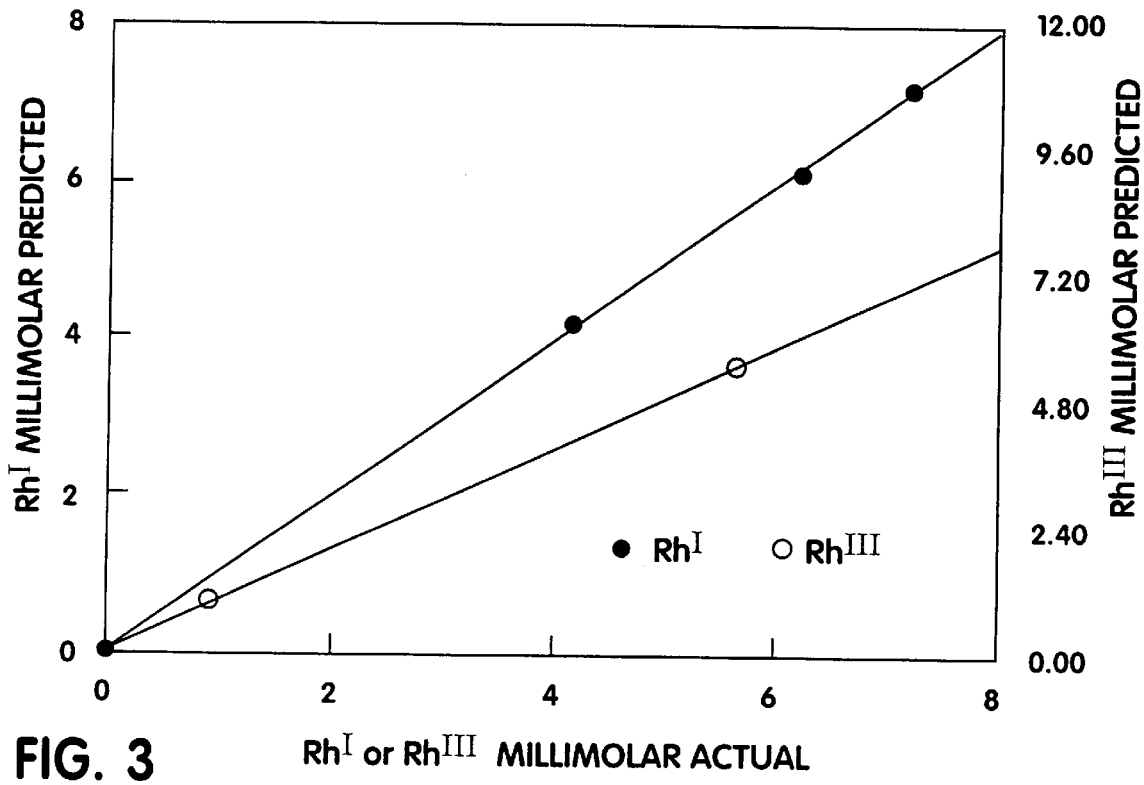
FIG. 3 is a correlation plot of actual vs. predicted values showing the validation of the laboratory mid-infrared calibration model for active rhodium species ($Rh^I$) and inactive rhodium species ($Rh^{III}$)

To validate the chemometric calibration models developed for rhodium on the online analyzer, solutions of known $Rh^I$ or $Rh^{III}$ concentration were prepared in the laboratory and subsequently injected into an online analyzer and quantified. The online analyzer is described in more detail in Example 1. The actual vs. predicted values are tabulated below in Table 3 and represented graphically in FIG. 3. Again, excellent agreement was observed.

TABLE 3

| SAMPLE # | ACTUAL $Rh^I$ (mMolar) | PREDICT $Rh^I$ (mMolar) | ACTUAL $Rh^{III}$ (mMolar) | PREDICT $Rh^{III}$ (mMolar) |
|---|---|---|---|---|
| 6 | 0.00 | −0.06 | | |
| 7 | 4.14 | 4.18 | | |
| 8 | 6.19 | 6.15 | | |
| 9 | 7.17 | 7.22 | | |
| 10 | | | 0.89 | 0.92 |
| 11 | | | 5.64 | 5.53 |

Another approach to verification of calibration models is to compare the concentration values predicted by online models during an actual process run with the concentration values obtained by independent off-line methods of analysis. These data can be obtained by manually sampling the continuous bench scale reactor at random periods, analyzing these samples by conventional instrumental and wet chemical methods and comparing the predicted values with the values predicted online at the exact time of manual sampling. Thus, methyl iodide concentration by online infrared analysis was compared with off-line gas chromatography using a capillary gas chromatograph equipped with a flame ionization detector. Off-line water concentration was measured by the Karl Fischer technique. Off-line rhodium concentration was measured by the inductively coupled plasma (ICP) technique after work up of the reactor sample. Off-line phosphine oxide concentration was measured by $^{31}P$ NMR. Off-line $I^-$ was measured by an iodide selective electrode or by titration with silver nitrate.

FIG. 4 contains several plots (FIGS. 4A–4E) for this method of verification. As each of the independent off-line methods of analysis (iodide selective electrode, gas chromatography, $^{31}P$ NMR, inductively coupled plasma spectroscopy and Karl Fischer water determination) all have separate and different accuracy and precision limits, the most meaningful interpretation of the correlations is to look for any consistent bias of overprediction or underprediction for each component. If no such bias exists, and if the data can be linearly fitted, then the R factor or correlation coefficient is a valid indicator of the degree of fit between respective online and off-line analyses. The R factors annotated in the graphs in FIG. 4 are all >0.99, indicating that online analysis by FTIR is at least as good as off-line measurements by other analytical methods. The great advantage of the online method is that the sampling frequency is at least 100 times greater compared to off-line methods and data is obtained in real time in terms of process control.

Figure 5:
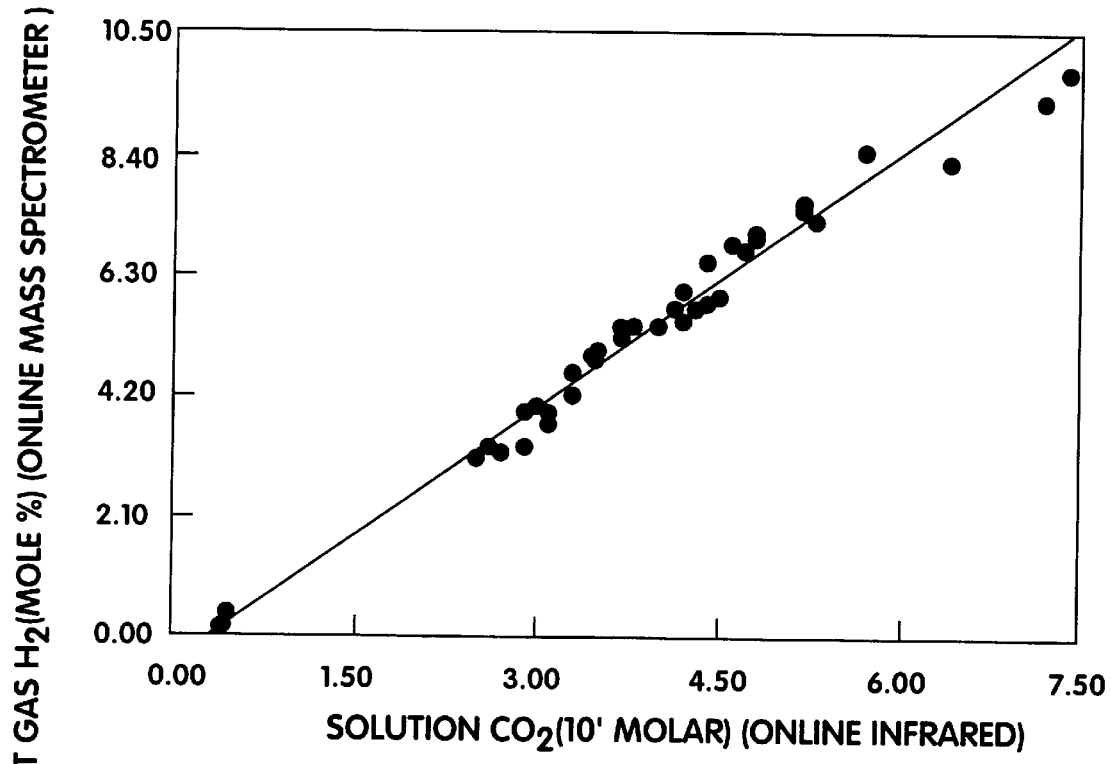
FIG. 5 is a correlation plot of bench scale reactor data for carbon dioxide solution concentration determined by online infrared vs. vent gas hydrogen concentration determined by mass spectrometry.
Figure 4A:
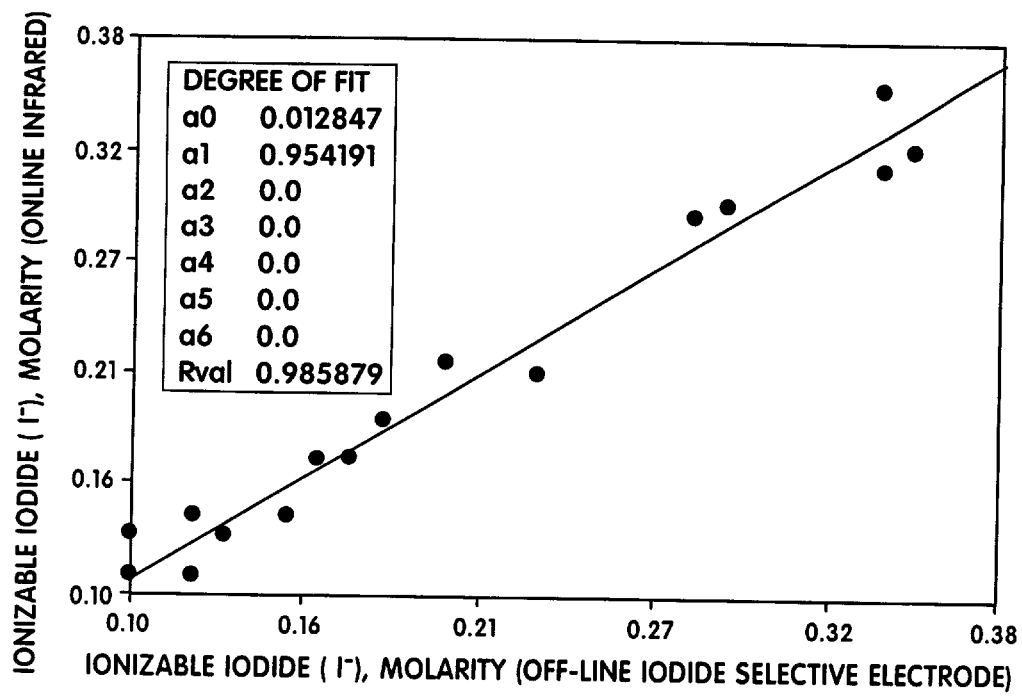
FIG. 4A is a correlation plot of analytical concentration values predicted by online infrared vs. analytical concentration values predicted by off-line iodide selective electrode for ionizable iodide ($I^-$)
Figure 4B:
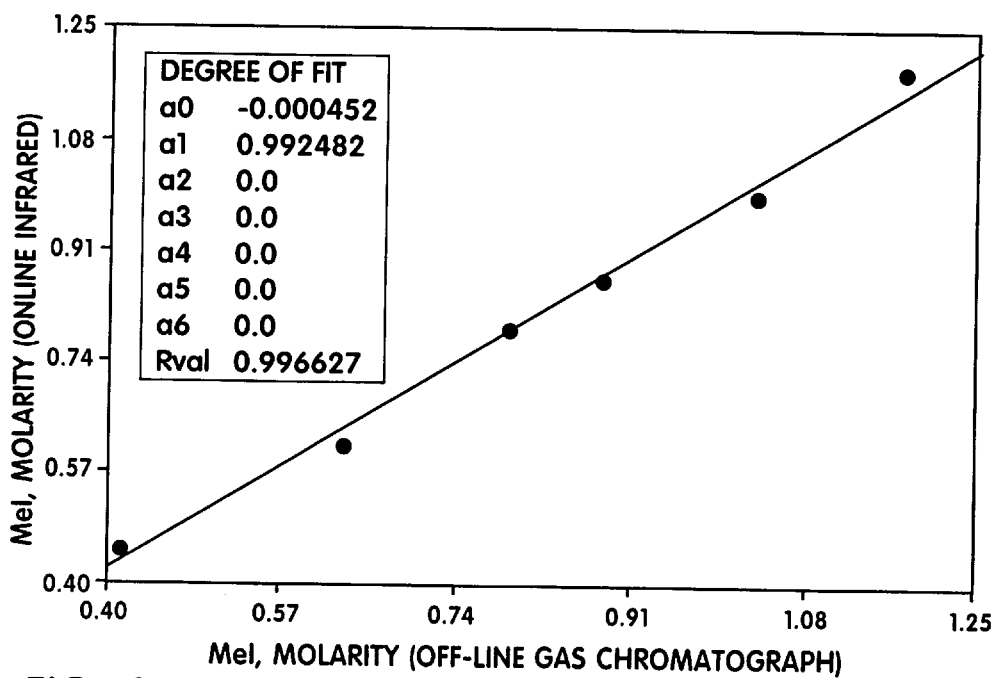
FIG. 4B is a correlation plot of analytical concentration values predicted by online infrared vs. analytical concentration values predicted by off-line gas chromatograph for methyl iodide (MeI)
Figure 4C:
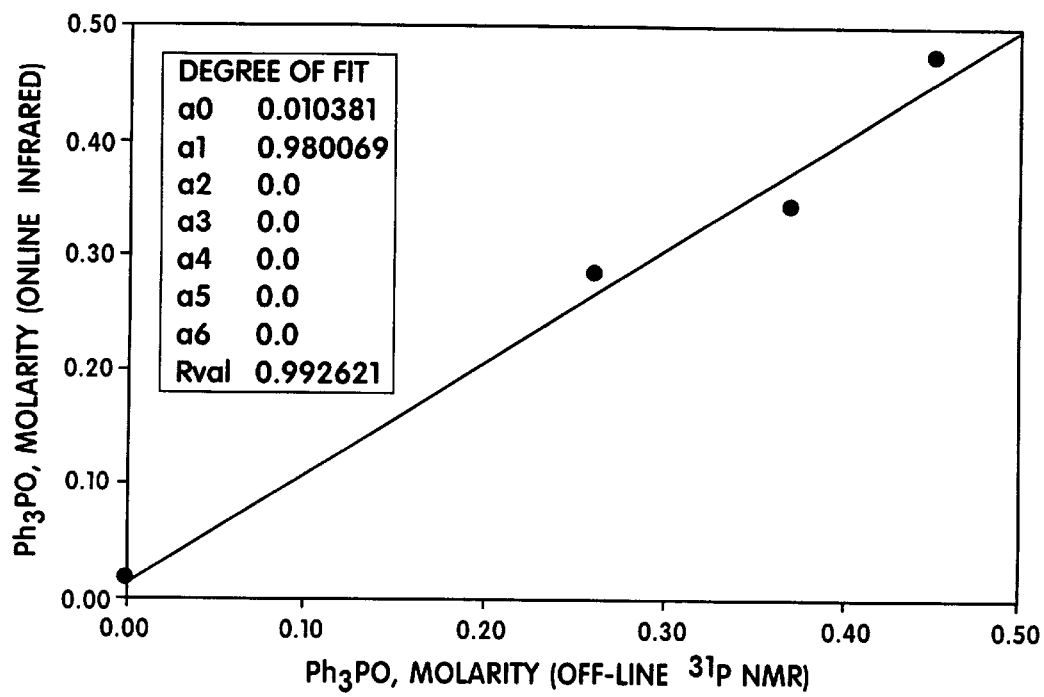
FIG. 4C is a correlation plot of analytical concentration values predicted by online infrared vs. analytical concentration values predicted by off-line $^{31}P$ NMR for triphenyl phosphine oxide ($Ph_3PO$)
Figure 4D:
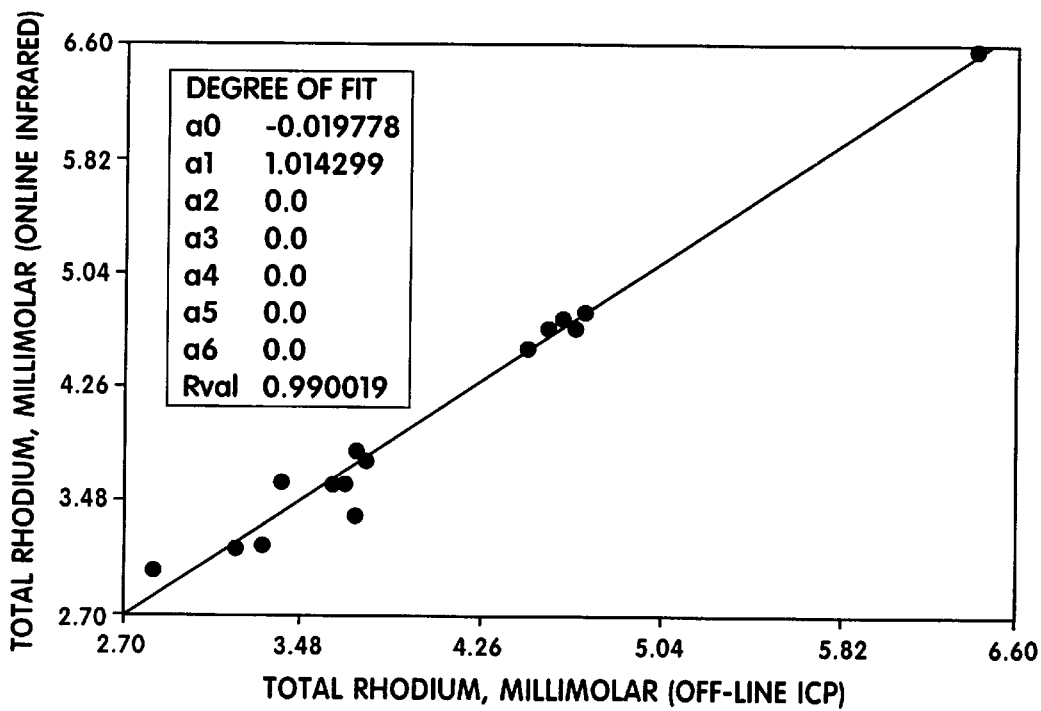
FIG. 4D is a correlation plot of analytical concentration values predicted by online infrared vs. analytical concentration values predicted by off-line inductively coupled plasma spectroscopy (ICP) for rhodium.
Figure 4E:
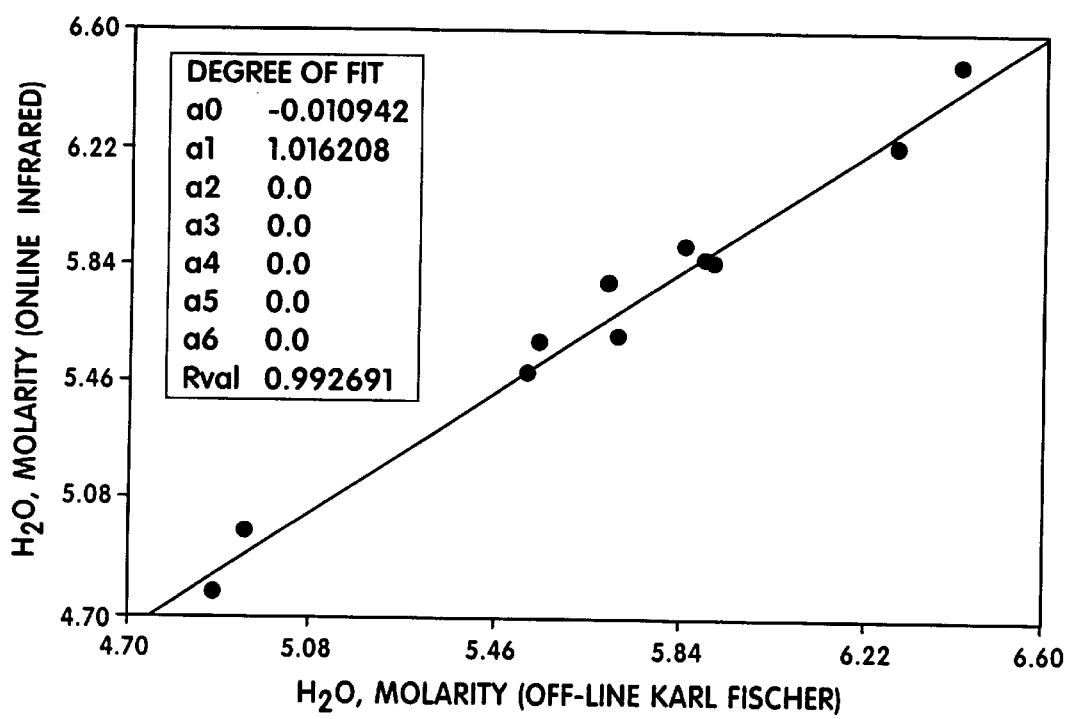
FIG. 4E is a correlation plot of analytical concentration values predicted by online infrared vs. analytical concentration values predicted by off-line Karl Fischer analysis for water.
Figure 6:
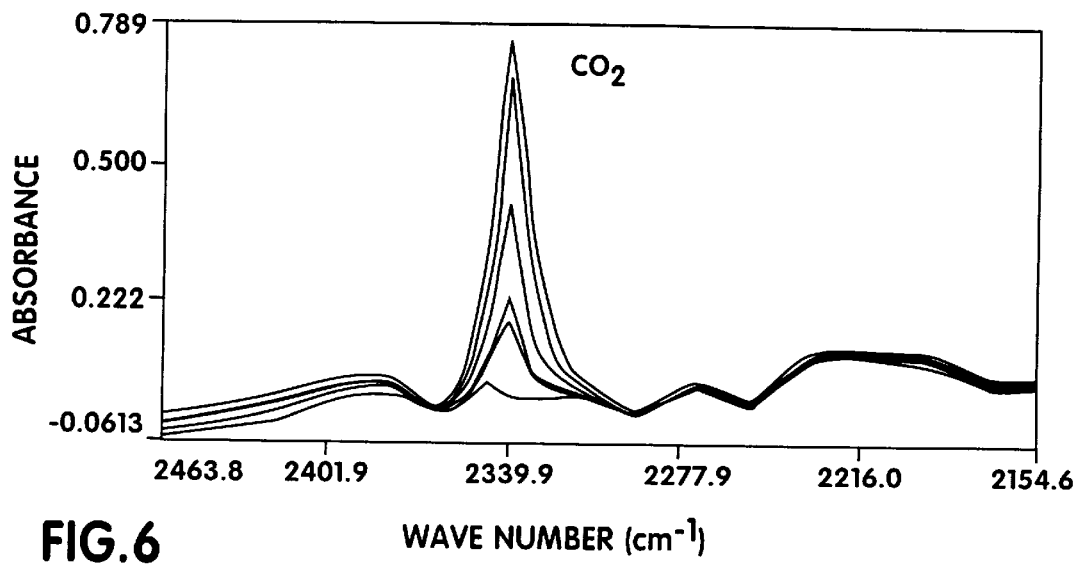
FIG. 6 is an overlay of online mid-infrared spectra showing the $CO_2$ peak intensity as it relates to reactor water concentration.

The monitoring process of the instant invention is also capable of measuring carbon dioxide concentration as a dissolved gas in the acetic acid reaction solution. Carbon dioxide production is inversely related to the selectivity of the process of acetic acid formation as it is produced along with hydrogen in the competing and undesirable water gas shift (WGS) reaction. The more conventional method of measuring the extent of the WGS reaction is by analyzing the hydrogen content of the reactor vent gas stream by mass spectrometry. The ability to quantify the WGS reaction by the same technique as for other reactor solution components, i.e. online infrared, allows it to be easily tied in to any process control loop built around online infrared analysis. In order to verify that carbon dioxide solution concentration as determined by online infrared analysis correlates with vent gas hydrogen concentration as determined by mass spectrometry, continuous bench scale reactor data for both methods were compared over a period of 44 hours run time during which water concentration was varied from 5.5 molar to 3 molar leading to significant changes in the extent of WGS reaction. The reactor was run under the conditions set out below:

Temperature: 185° C.
Pressure: 400 psig
Methyl iodide concentration: 0.75 Molar
Triphenyl phosphine oxide concentration: 0.5 Molar
Rhodium concentration: 5.5 Millimolar
Methanol feed rate: 220 g/hr The correlation plot in FIG. 5 shows excellent agreement between the two techniques. FIG. 6 contains several overlaid mid-infrared spectra showing the changes in intensity of the $CO_2$ peak.

EXAMPLES

The following detailed operating examples illustrate the practice of the invention in its most preferred form, thereby enabling a person of ordinary skill in the art to practice the invention. The principles of this invention, its operating parameters and other obvious modifications thereof will be understood in view of the following detailed procedure.

Example 1

A continuous 2 liter bench scale reactor was run for several days under the conditions set out below:

Reactor temperature=187° C.–189° C.
Reactor pressure=400 psig (130 psig CO)
Methyl iodide concentration=1.0 molar
Water concentration=3.5 molar
Rhodium concentration=6.5 millimolar
Triphenyl phosphine oxide concentration=0.5 molar
Methanol feed rate=320 g/hr.

The process was automatically controlled from data generated by an online infrared analyzer. The analyzer used in this example was a single source, dual detector, dual cell model and was comprised of a sample compartment and an electronics compartment. The sample compartment contained the cells, tubing to allow reactor solution to flow through the cells, a flowmeter, filter and heater. All parts in contact with process solution were fabricated from Hastelloy™ B2. The electronics compartment contained the single polychromatic infrared light source, the interferometer, the detectors, analog input and output cards, and associated peripherals such as power supply, and other components which control the analyzer. The two compartments were connected via infrared transparent windows which allowed light to pass from the source, through the cells and back to the detectors.

Reactor solution flowed continuously through the analyzer and was returned to the reaction system via the low pressure flash tank. Mid- and extended mid-infrared analyses were sequentially carried out using a 0.075 mm pathlength cell and a 2 mm pathlength cell, respectively. Infrared light passing through the mid-infrared cell was deflected to a deutero triglycine sulfide (DTGS) detector and light passing through the extended mid-infrared cell was deflected to an indium arsenide (InAs) detector. Sapphire windows were used in both cells and the sample cabinet was maintained at a temperature of 100° C.

The same 2 liter bench scale reactor and the same online infrared analyzer as discussed herein in Example I were used for all subsequent examples discussed herein.

Figure 7:
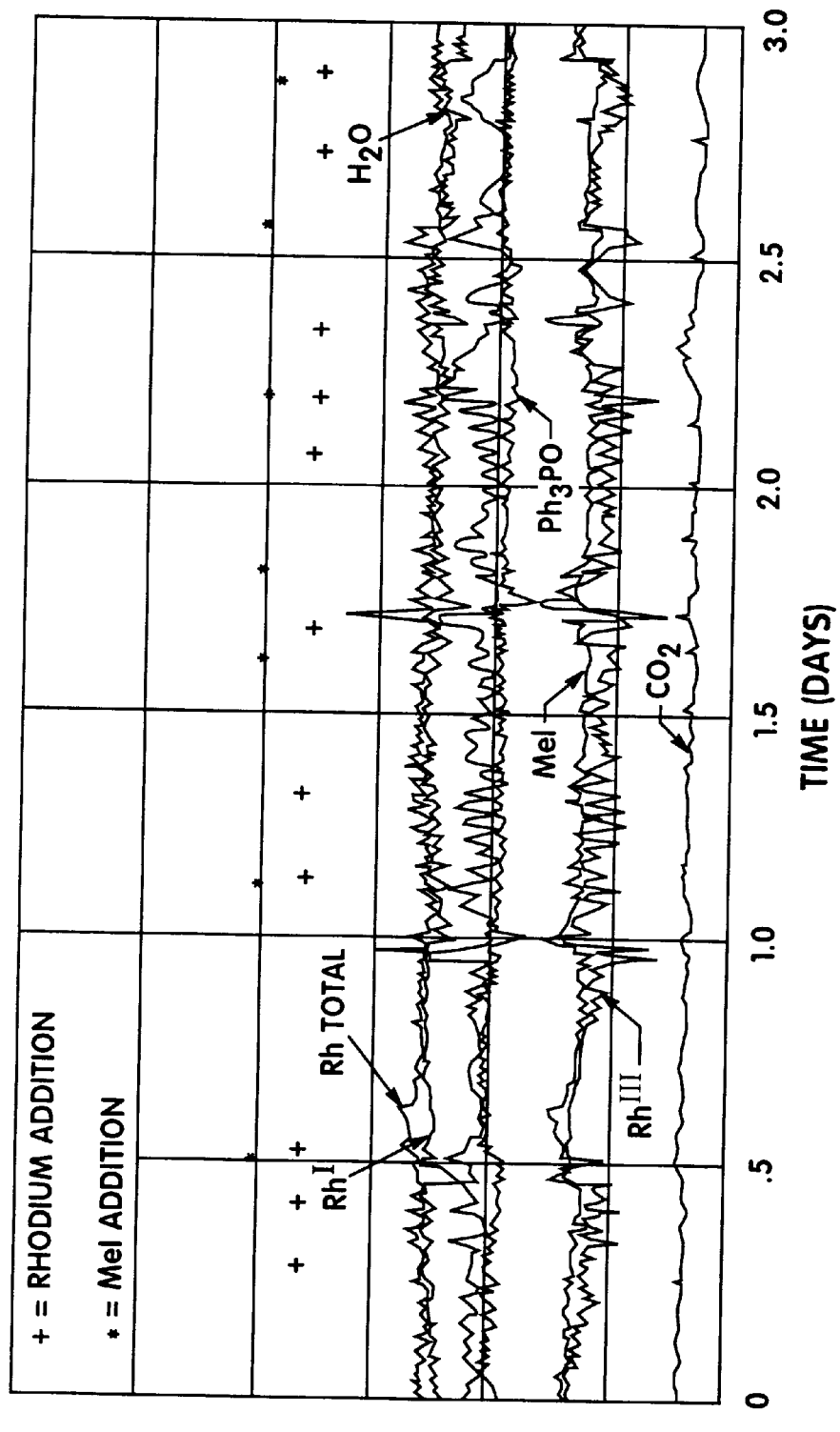
FIG. 7 is a multi component trend file containing three days of run time data for seven reactor solution components.

A multi component trend file containing three days of run time data is shown in FIG. 7. The concentrations of seven reactor solution components are trended in this chart. Each of the seven trend lines is composed of more than 2000 data points. No concentration values are given on the Y axis, as each reactor solution component has its own scale. FIG. 7 is merely representative of the trends for each component. Also plotted on this chart are the times at which methyl iodide (MeI) and rhodium were added. The method of controlling component addition for rhodium and methyl iodide was slightly different than the method for controlling the addition of water. Rhodium and methyl iodide are not formally consumed in the process, but some losses did occur because of precipitation of rhodium and because of losses downstream of the reaction section for both rhodium and methyl iodide. Water, on the other hand, is consumed in the process by the water gas shift reaction.

The component concentrations measured by the analyzer were converted to proportional 4–20 mA signals. Component addition was then controlled by a Process Logic Controller (PLC) based on these signals. Signals were sent to the PLC every 2 minutes averaged over the life of the run, but the concentration was evaluated as a rolling average over a one hour time period. In the case of rhodium or methyl iodide, if the average molar (or millimolar) concentration value over the rolling time period fell below the preset control limits set out below, a volume sufficient to return the component to its normal control limit of rhodium solution or methyl iodide was automatically added to the system. As water was rapidly consumed in the process, no rolling time period was used. Instead, a water pump operated continually and the pump rate was automatically adjusted in response to every data point to maintain water within preset control limits. The lower control limits used in this example are shown below in Table 4. The reaction consumes the analyzed reactant components over time, and thus upper control limits are not required. Over the three day test period it was not necessary to add triphenyl phosphine oxide.

TABLE 4

| COMPONENT | NORMAL CONTROL LIMIT | LOWER CONTROL LIMIT |
|---|---|---|
| Water | 3.5 molar | 3.2 molar |
| Methyl Iodide | 1.0 molar | 0.9 molar |
| Rhodium | 6.5 millimolar | 6.0 millimolar |
| $Ph_3PO$ | 0.50 molar | 0.45 molar |

It should be noted that the use of an average concentration and the generous control limits are not solely a function of precision and accuracy of the analyses. In a reaction system of this kind in which there is continual cycle of solution between the reactor and flash tank, the solution component concentration may not be at steady state in either vessel. The use of a rolling time average thus allows for these effects to be buffered and prevents unnecessary component additions.

It can be seen from FIG. 7 that use of infrared analyzer data allowed excellent process control. Only two sharp spikes were observed over the three-day period which are believed to have been caused by momentary electronic noise. Reaction rate is a direct function of the concentration of rhodium, methyl iodide, $H_2O$ and (when present) triphenyl phosphine oxide. The ability to continuously monitor and tightly control concentrations of these components in the reactor allows productivity to be maximized, system upsets to be identified quickly and addressed, and rhodium precipitation to be minimized. In addition, a tight control of reactor water concentration results in acetic acid product with a minimal variation in water content, in turn resulting in more stable operation of the dryer column to remove water from the acetic acid.

Figure 8:
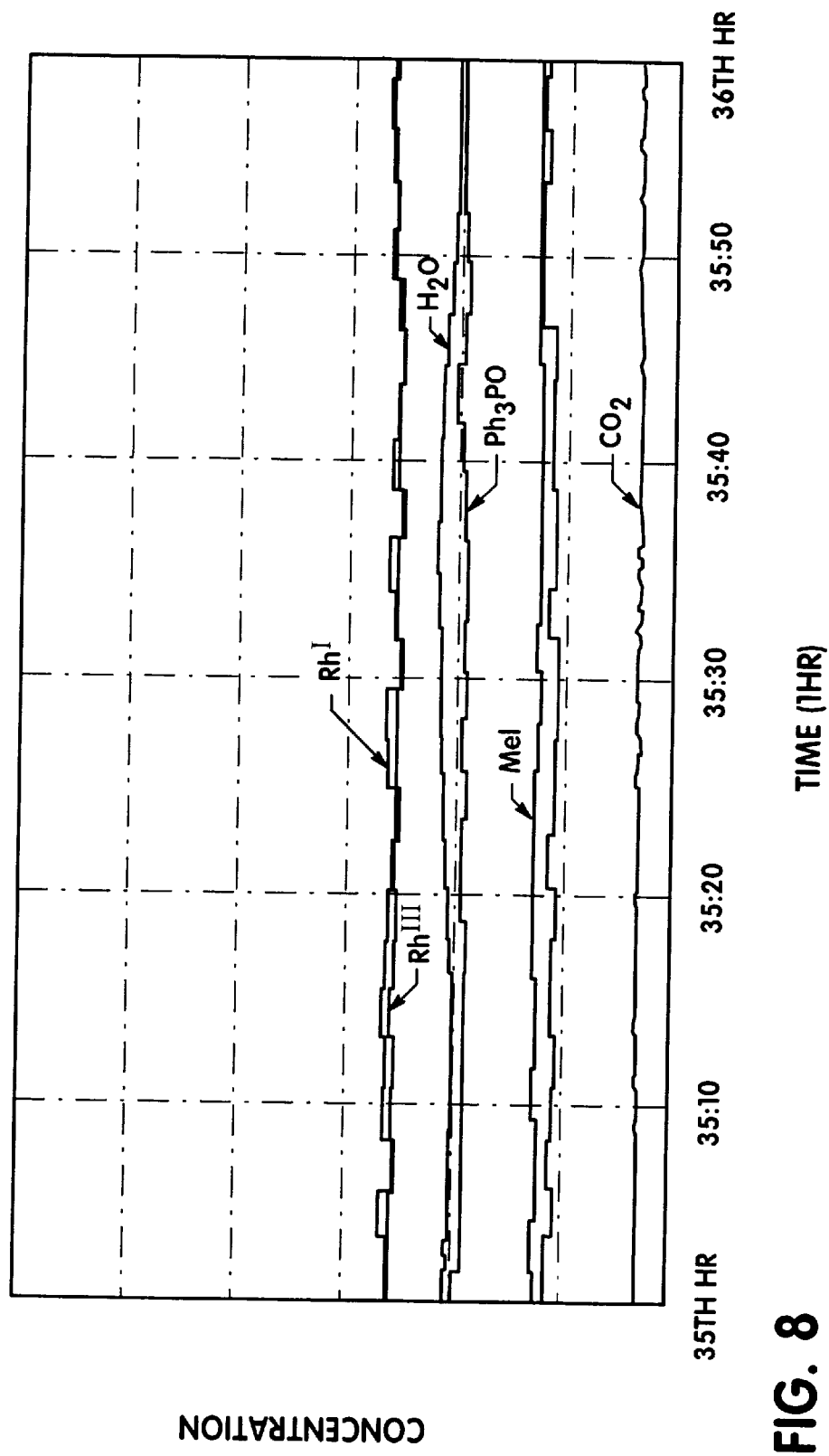
FIG. 8 is an expanded view of a one hour time segment of the trend file of FIG. 7.

FIG. 8 shows an expanded version of FIG. 7 in which a one-hour time segment (the $35^{th}$ hour of the three day run) of the reaction is represented. This particular segment was chosen because it contains no component additions (other than water) and because it represents a period of very stable operation when reactor level was under very tight control. Thus, any data scatter in this period should predominately reflect measurement precision. The highest and lowest concentrations for the seven components on this trend chart for the one-hour period (30 data points) are shown below in Table 5.

TABLE 5

| COMPONENT | HIGH | LOW |
| --- | --- | --- |
| $Rh^I$ | 4.46 | 4.40 |
| $Rh^{III}$ | 1.91 | 1.96 |
| Rh total | 6.62 | 6.60 |
| Triphenyl Phosphine Oxide | 0.50 | 0.49 |
| Water | 3.48 | 3.27 |
| $CO_2$ | 5.40 | 5.31 |
| Methyl iodide | 1.03 | 1.03 |

Example 2

The form of rhodium, i.e. $Rh(CO)_2I_2^-$ ($Rh^I$) or $Rh(CO)_2I_4^-$ ($Rh^{III}$) and the stability of rhodium to precipitation in acetic acid reactor solution is a function not only of solution chemical composition, but also of physical variables such as stirring rate. In conventional liquid reactors used by acetic acid manufacturers practicing methanol carbonylation technology, stirring is considered necessary to maintain solution homogeneity. This may be particularly true for dispersion of carbon monoxide in solution, as isolated pockets of reactor solution without sufficient dissolved carbon monoxide may be prone to precipitate rhodium.

In the experiment outlined below, conditions used in the continuous bench scale reaction reactor were as follows:

Temperature=185° C.

Pressure=400 psig

Rhodium=6 millimolar

Water=7 molar

Methyl Iodide=0.8 molar

Triphenyl phosphine oxide=0.0 molar

Methanol feed rate=220 g/hr.

Figure 9:
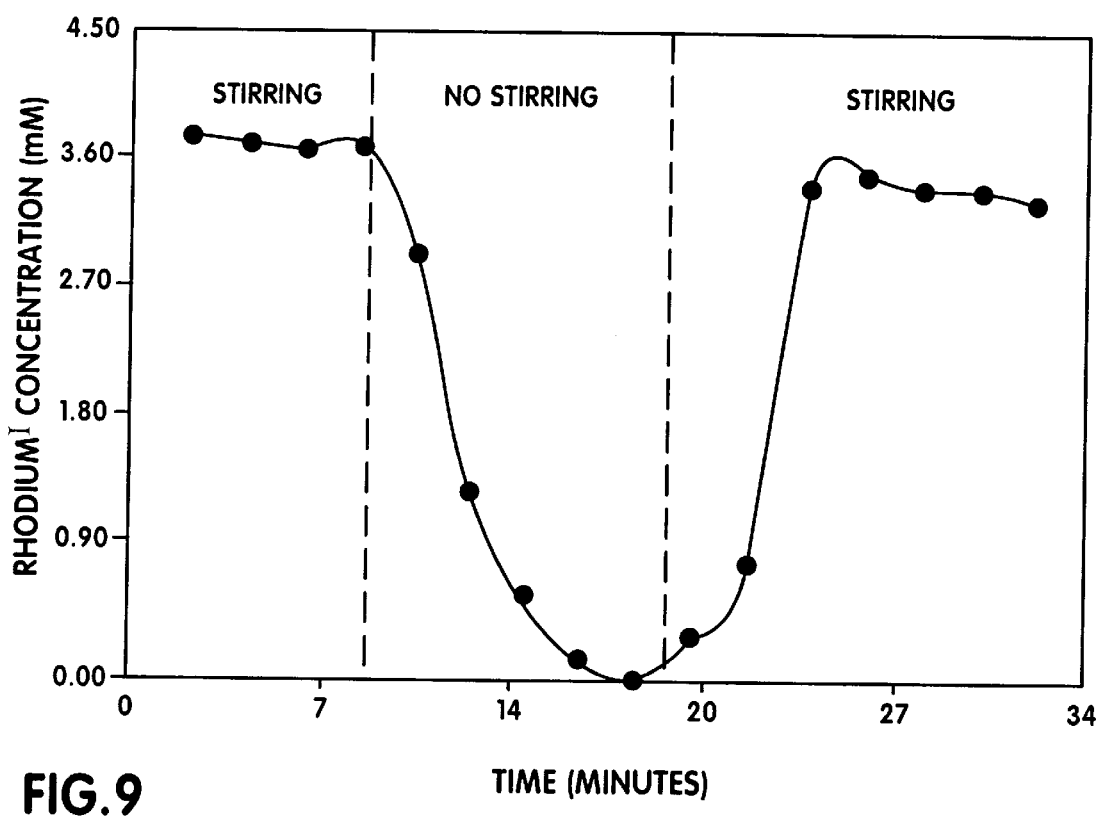
FIG. 9 is a plot of continuous bench scale reactor online infrared data for active rhodium species concentration over time as a function of agitation within the reactor solution.
Figure 10:
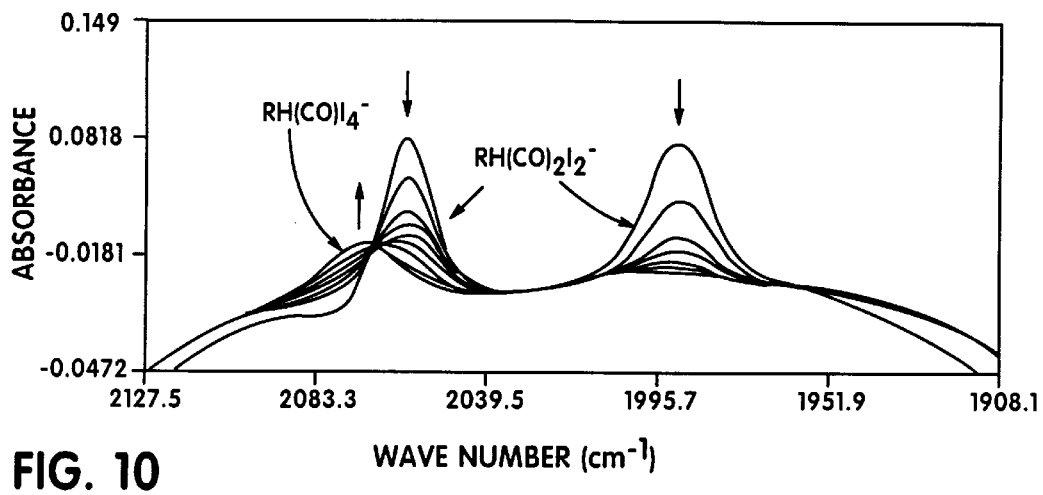
FIG. 10 is an overlay of online mid-infrared spectra showing the existence of an inactive species of rhodium, $Rh(CO)I_4^-$, in addition to $Rh^I$ as a result of the absence of agitation.

Over the one hour test period, the reactor agitator was turned off one time for several minutes and then back on again to determine the effect on rhodium. It was noted that $Rh^I$ rapidly and completely disappeared in the unagitated solution, but equally rapidly reappeared on reestablishment of agitation as exemplified in FIG. 9. Examination of the analyzer spectra showed that concomitant formation of $Rh(CO)I_4^-$, hereafter referred to as $Rh^{III}$ mono, occurred. Overlaid infrared spectra illustrating the appearance of this species are shown in FIG. 10. The presence of $Rh^{III}$ mono is indicative of carbon monoxide starved conditions. It was shown by manually sampling the reactor and laboratory infrared analysis, that $Rh^{III}$ mono was not forming in the reactor but rather in the transfer lines to the analyzer or in the analyzer itself. This formation was occurring due to continuing reaction (and carbon monoxide consumption without the possibility of replenishment) in the transfer lines. Under normal well-stirred conditions there is sufficient dissolved carbon monoxide in the reactor solution such that $Rh^{III}$ mono does not form in the transfer lines.

This result shows that another advantage of the present invention in terms of process control is the use of online infrared analyzer data as a diagnostic tool for stirrer problems or as a tool to optimize agitation rate for various solution compositions and reactor conditions.

Example 3

It has previously been deduced that the form of active rhodium for acetic acid formation is $Rh^I$. In addition, this form is also more stable relative to $Rh^{III}$ in terms of precipitation. Thus there are substantive advantages to be gained in terms of catalyst usage, required catalyst concentration and smooth process operation if a real time knowledge of $Rh^I$ in the acetic reactor can be obtained. Furthermore, the availability of such knowledge allows the effect of changing conditions or of testing new technology on catalyst sensitivity and catalyst form to be rapidly and accurately assessed. Analysis of samples obtained manually from the reactor by the conventional method of elemental analysis or by the method of laboratory infrared analysis described hereinabove, while allowing an accurate determination of total rhodium does not allow the $Rh^I/Rh^{III}$ ratio present in the reactor at time of sampling to be obtained. The methods of elemental analysis such as inductively coupled plasma analysis (ICP) or atomic absorption (AA) are species indiscriminate. Laboratory infrared analysis is capable of distinguishing between and quantifying $Rh^I$ and $Rh^{III}$, but $Rh^I$ rapidly oxidizes to $Rh^{III}$ in traces of air and thus the $Rh^I/Rh^{III}$ ratio measured by this method is rarely representative of the ratio in the reactor at time of sampling. The measured ratio is subject to factors such as time between sampling and analysis, and degree of air contamination on sampling and subsequent handling. Thus the only method of obtaining a knowledge of the $Rh^I/Rh^{III}$ ratio in the reactor is online infrared analysis.

Figure 11:
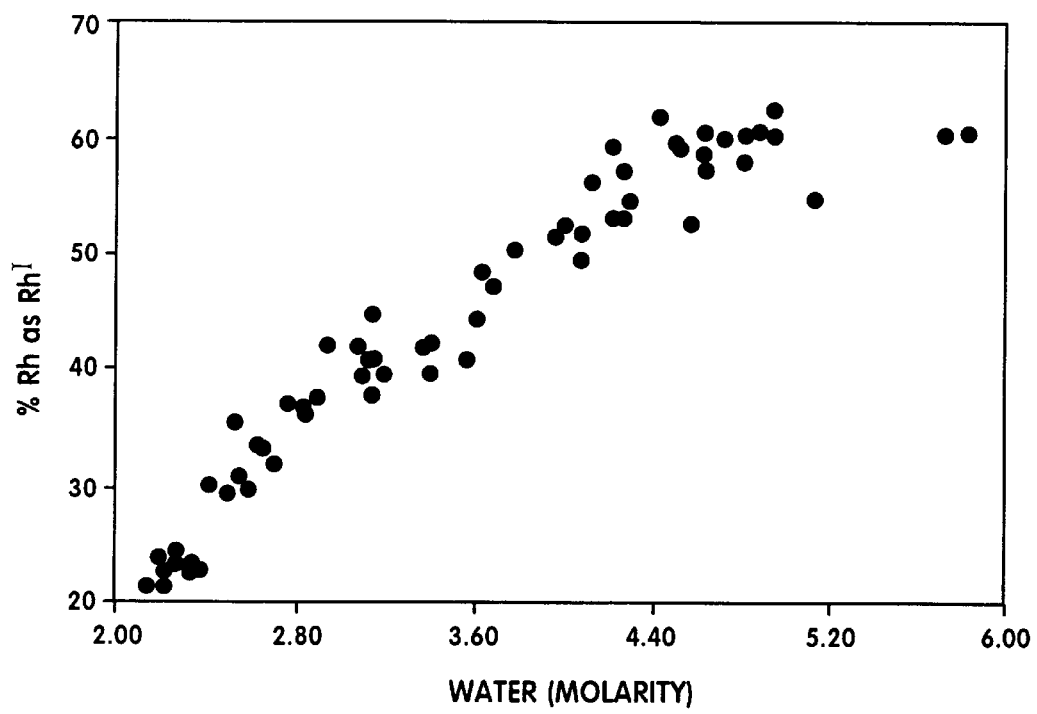
FIG. 11 is a correlation plot of continuous bench scale reactor online infrared data for $Rh^I$ concentration as a function of water.

An illustration of the effect of water on $Rh^I$ concentration is shown in FIG. 11. Over a four day period, water was varied from 2 molar to 6 molar under reactor conditions as outlined below. The sampling and analysis frequency was approximately 30 times per hour over the four day period.

Temperature=185° C.

Pressure=400 psig

Rhodium=4.8–6.4 molar

Triphenyl phosphine oxide=0.50 molar

Methyl Iodide=0.8 molar

Methanol feed rate=180 g/hr

Figure 12A:
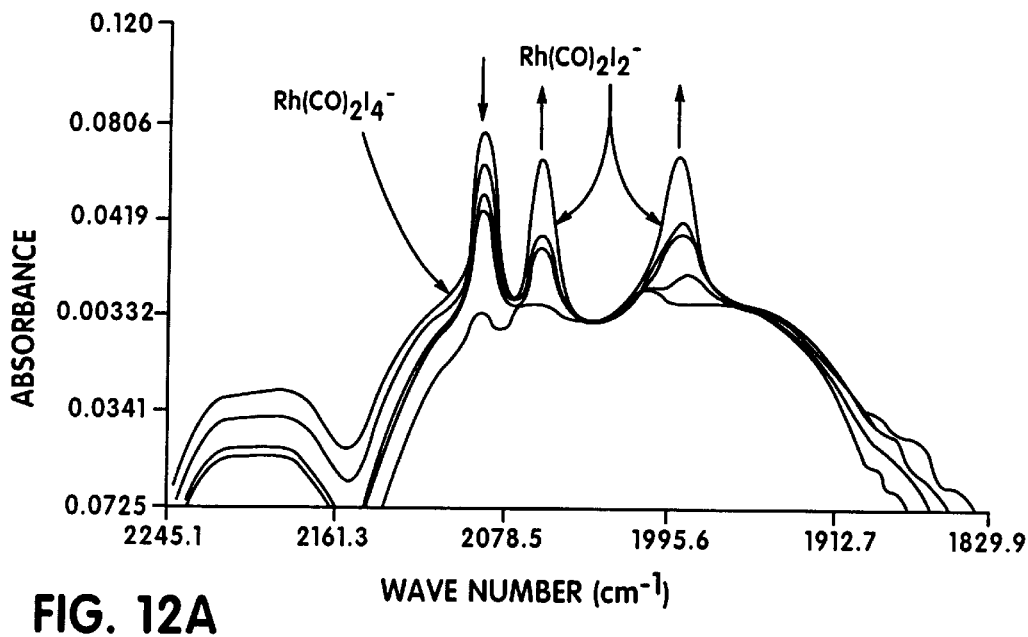
FIG. 12A is an overlay of online mid-infrared spectra for rhodium.
Figure 12B:
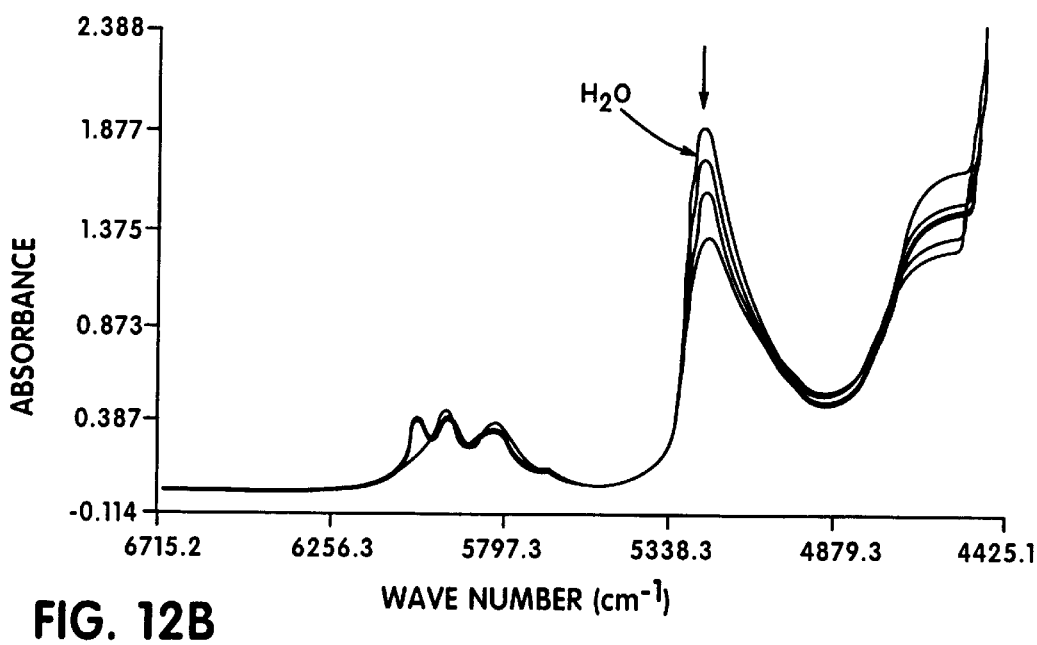
FIG. 12B is an overlay of online extended mid-infrared spectra for water.

FIG. 11 represents about 60 data points culled from the four days of online analyzer run time data. These data points were selected for clarity and are representative of the trend file. The dependence of $Rh^I$ on water is clearly evident. This effect is illustrated spectroscopically in FIGS. 12A and 12B in which overlaid online spectra of rhodium in the mid-infrared region and of water in the extended mid-infrared region are presented. The vertical up and vertical down arrows of FIG. 12 and subsequent Figures show the general increasing and decreasing concentration trends as represented by peak height for each component shown in each Figure. Availability of this kind of data can allow a process to be tailored to achieve optimal balance of methanol feed rate, rhodium consumption and reactor water concentration.

The ability to correlate the concentrations of $Rh^I$ and water shown in this example demonstrates an advantage of the invention. The absolute values of % Rh as $Rh^I$ on the Y axis in FIG. 11 are not optimized, as they are also a function of many other variables such as methanol feed rate, presence of additive mixtures, and the like.

Example 4

Figure 13:
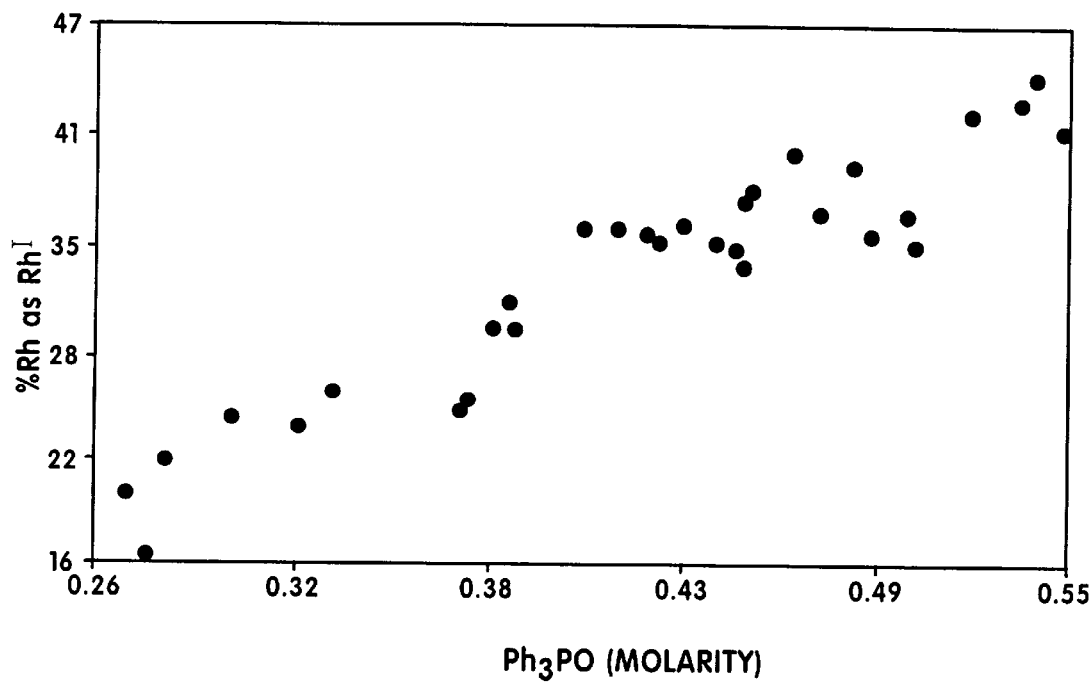
FIG. 13 is a correlation plot of continuous bench scale reactor online infrared data for active rhodium species ($Rh^I$) concentration as a function of triphenyl phosphine oxide ($Ph_3PO$) concentration.

An illustration of the effect of triphenyl phosphine oxide concentration on $Rh^I$ concentration as determined by online infrared analysis is shown in FIG. 13. Over an eight-hour period in the continuous bench scale reactor, triphenyl phosphine oxide concentration was increased from 0.25 molar to 0.55 molar under reactor conditions as outlined below:

Temperature=185° C.

Pressure=400 psig

Water=2.8 molar

Total rhodium=3.5 millimolar

No Methanol feed

Figure 14:
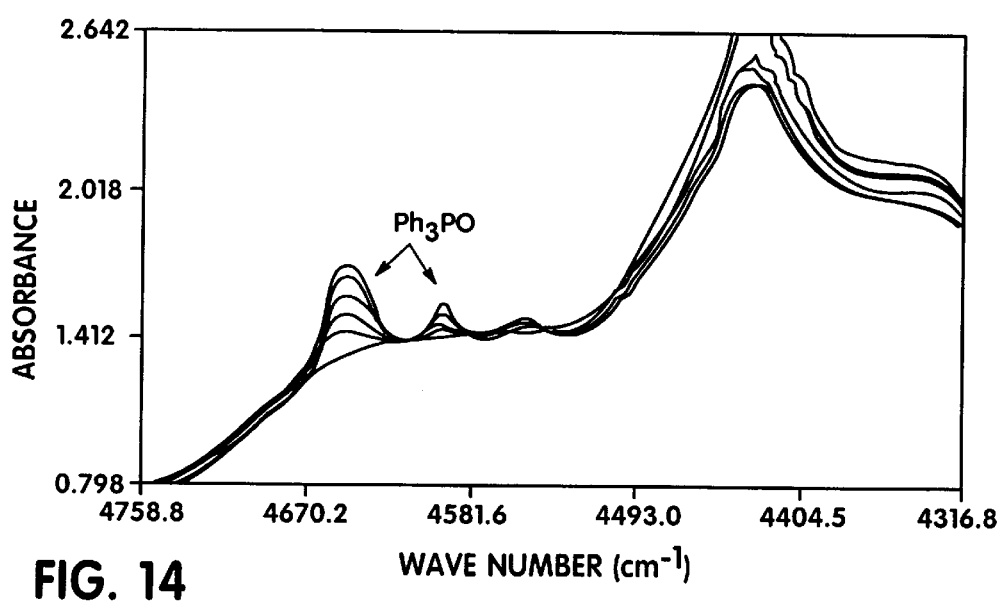
FIG. 14 is an overlay of online extended mid-infrared spectra for triphenyl phosphine oxide ($Ph_3PO$)

FIG. 13 contains about 35 data points removed from the trend file for clarity. As in the case of water in Example 3, a direct dependence of Rh as $Rh^I$ on triphenyl phosphine oxide concentration is observed. FIG. 14 contains several overlaid spectra from the extended mid-infrared region showing the increase in triphenyl phosphine oxide concentration. As in the previous example, this example serves to show the intimate correlations between reactor solution components that can be deduced from online infrared analysis. This example shows that the triphenyl phosphine oxide concentration can be tuned to achieve a desired $Rh^I$ concentration. As in the previous example, the ability to determine the absolute value of % Rh as $Rh^I$ as shown in FIG. 13 demonstrates an advantage of the invention and is only a function of the specific reactor conditions used in this example.

Example 5

The water gas shift reaction involving the rhodium catalyzed formation of carbon dioxide and hydrogen gas from carbon monoxide and water is an undesirable side reaction in acetic acid processing via methanol carbonylation. It increases carbon monoxide usage rates and decreases catalyst stability. The ability to precisely and accurately monitor on a frequent basis the components that influence the WGS rate can lead to appropriate algorithms to be built into process control to allow optimal run conditions to be achieved and maintained. Maintenance of such conditions can lead to higher production rates, lower raw material usage rates and lower catalyst usage rates. The effect of several reactor solution components on WGS rate are shown in the experiments below.

(a) In a continuous bench scale reactor experiment under reactor conditions given below, water concentration was allowed to decrease from 7 molar to 5 molar over a three-hour period and the effect on the WGS reaction (as a function of solution $CO_2$) was tracked by online infrared analysis. Sampling and analysis frequency was approximately 30 times per hour.

Temperature=185° C.

Pressure=400 psig

Triphenyl phosphine oxide=0.30 molar

Rhodium=10.5 molar

Methyl iodide=0.85 molar

Methanol feed rate=320 g/hr

Figure 15:
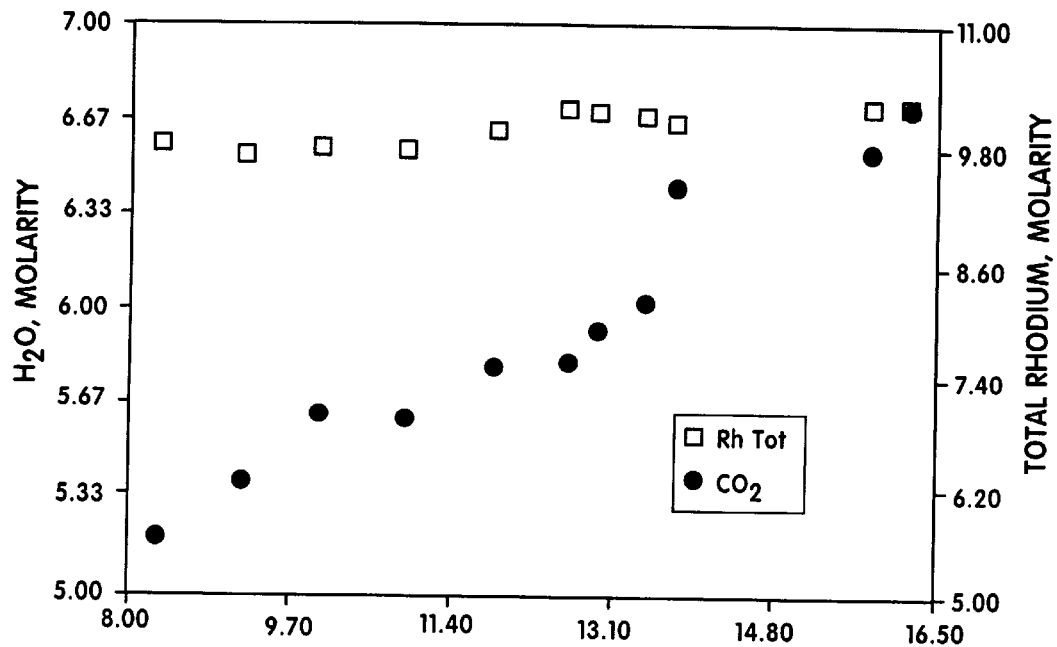
FIG. 15 is a correlation plot of continuous bench scale reactor online infrared data for the water gas shift reaction represented by change in $CO_2$ content at constant rhodium concentration, as a function of water concentration.

The data are presented in graphical format in FIG. 15 and show that at constant rhodium concentration, the WGS rate increases linearly with water concentration.

(b) In this experiment reactor conditions were as follows:

Temperature=185° C.

Pressure=400 psig

Triphenyl phosphine oxide=0.0 molar

Methyl iodide=0.0–0.2 molar $I^-$=0.4–0.6 molar $H_2O$=3.5 molar

No Methanol feed

Figure 16:
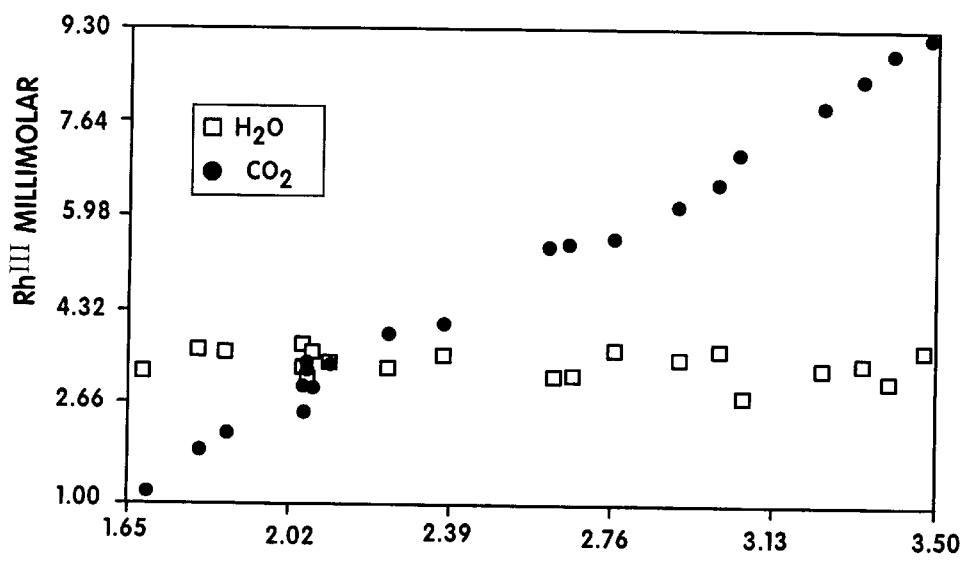
FIG. 16 is a correlation plot of continuous bench scale reactor online infrared data for the water gas shift reaction represented by change in $CO_2$ content as a function of rhodium concentration.
Figure 17:
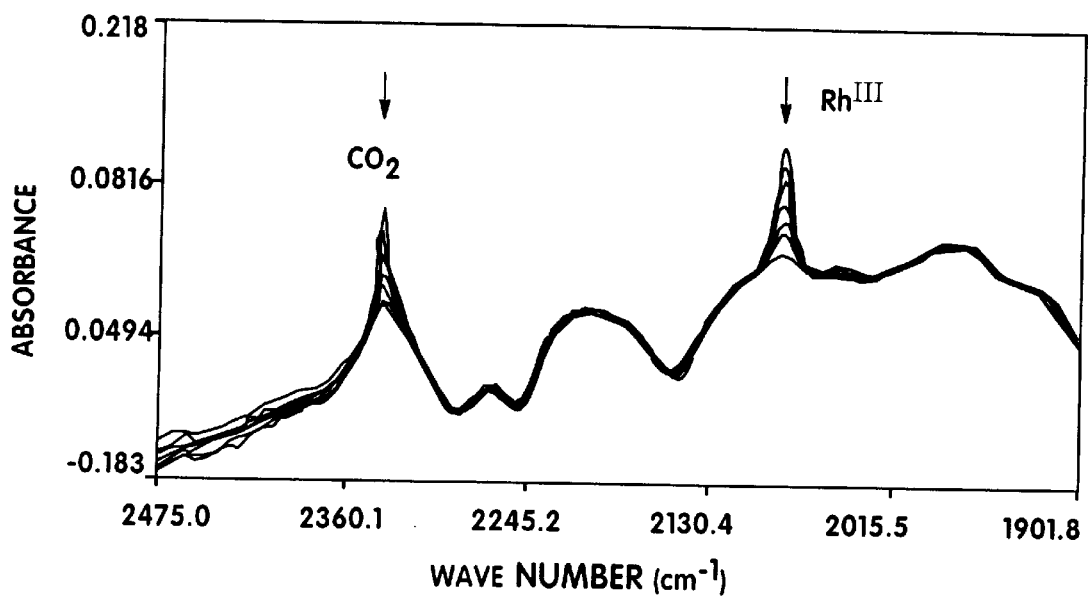
FIG. 17 is an overlay of online infrared spectra for water gas shift reaction represented by change in $CO_2$ content as a function of rhodium concentration.

In this experiment, rhodium was allowed to decay under conditions which are highly undesirable for catalyst stability. This decay was allowed to occur at a constant water concentration to examine the effect of rhodium concentration on WGS rate. The data are presented in graphical format in FIG. 16 and in overlaid spectral format in FIG. 17. Both figures show the linear decrease in solution carbon dioxide with decreasing rhodium concentration.

Figure 18:
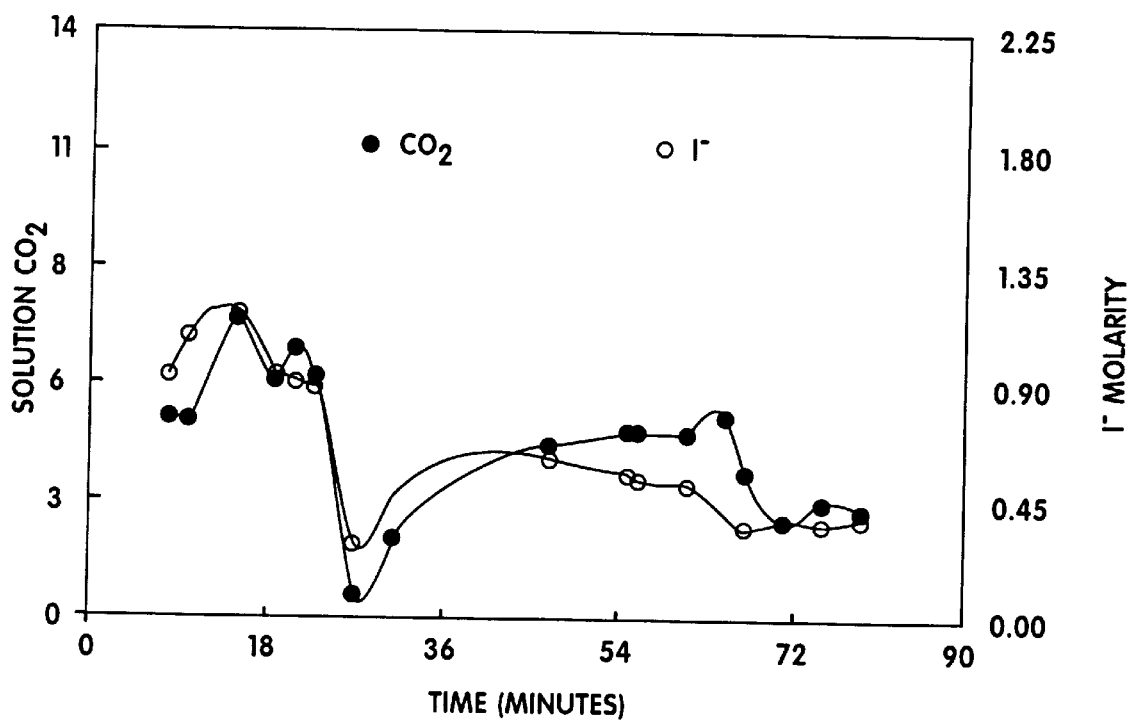
FIG. 18 is a correlation plot of continuous bench scale reactor online infrared data for the water gas shift reaction represented by change in $CO_2$ content as a function of ionizable iodide ($I^-$) concentration.

(c) This experiment involves reactor startup, i.e., from ambient conditions and no raw material feeds to process conditions with established feeds. Reactor solution component concentrations can vary considerably during startup due to shifts in various dependent equilibria until stable operating conditions are established. Data was chosen from a single representative ninety-minute period when water and rhodium concentration remained relatively constant but the methyl iodide/ionizable iodide ($I^-$) ratio varied considerably. This allowed the effect of $I^-$ on WGS rate to be determined. The plot shown in FIG. 18 indicates that solution carbon dioxide closely tracks $I^-$ concentration. This is consistent with the mechanism of the WGS reaction and again shows the advantage of employing online infrared data in tracking and potentially controlling an acetic process.

While the present invention has been illustrated by the description of an embodiment thereof, and while the embodiment has been described in considerable detail, it is not intended to restrict or in any way limit the scope of the appended claims to such detail. Additional advantages and modifications will readily appear to those skilled in the art. For example, a single cell or two cell infrared system may be successfully utilized in the present invention. Moreover, an iridium-catalyzed carbonylation system may be used in accordance with the principles of the present invention rather that a rhodium-catalyzed carbonylation system. The invention in its broader aspects is therefore not limited to the specific details, representative apparatus and method and illustrative examples shown and described. Accordingly, departures may be made from such details without departing from the scope or spirit of applicant's general inventive concept.

What is claimed is:

1. A method of effecting process control in a reaction for the production of acetic acid, comprising:

collecting a sample of an acetic acid reaction mixture containing at least methyl iodide, water, methyl acetate and an active catalyst species of a catalyst selected from the group consisting of rhodium and iridium;

measuring the at least the concentrations of methyl iodide, water, and the active catalyst species in an infrared analyzer; and adjusting the concentration of at least methyl iodide, water and the active catalyst species in the acetic acid reaction mixture in response to the measured concentrations of methyl iodide, water, and active catalyst species.

2. The method of claim 1 wherein the infrared analyzer is a Fourier Transform infrared spectrometer.

3. The method of claim 1 further comprising measuring the concentration of methyl iodide in an infrared cell operating in a range selected from the group consisting of a mid-infrared region, an extended mid-infrared region, and combinations thereof.

4. The method of claim 1 further comprising measuring the concentration of water in an infrared cell operating in a range selected from the group consisting of a mid-infrared region, an extended mid-infrared region, and combinations thereof.

5. The method of claim 1 further comprising measuring the concentration of active catalyst species in an infrared cell operating in a mid-infrared region.

6. The method of claim 5 wherein the active catalyst species is of a rhodium catalyst.

7. The method of claim 1 wherein adjusting the concentration of at least methyl iodide, water and the active catalyst species in the acetic acid reaction mixture produces a substantially constant concentration for each of methyl iodide, water, and active catalyst species during the manufacture of acetic acid.

8. The method of claim 7 wherein the active catalyst species is of a rhodium catalyst.

9. The method of claim 1 wherein the frequency of measuring the concentration of methyl iodide, water, and the active catalyst species is at least about 30 times per hour.

10. The method of claim 1 further comprising controlling the sample temperature in a range between about 20° C. and about 130° C.

11. The method of claim 1 wherein the infrared analyzer contains a first cell operating in a mid-infrared region and a second cell operating in an extended mid-infrared region.

12. The method of claim 11 wherein the infrared analyzer utilizes a single polychromatic light source.

13. The method of claim 1 further comprising transmitting the measured concentrations to a control unit.

14. The method of claim 1 wherein the acetic acid reaction mixture contains a Group 15 oxide of the formula $R_3M=O$, wherein M is an element from Group 15 of Periodic Table and each R is independently a substituted or unsubstituted alkyl, aryl, aralkyl or alkaryl group.

15. The method of claim 14 further comprising measuring the concentration of the Group 15 oxide in the infrared analyzer.

16. The method of claim 15 further comprising measuring the concentration of Group 15 oxide in an infrared cell operating in a range selected from the group consisting of a mid-infrared region, an extended mid-infrared region, and combinations thereof.

17. The method of claim 15 further comprising adjusting the concentration of the Group 15 oxide.

18. The method of claim 14 wherein M is phosphorus.

19. The method of claim 18 wherein $R_3M=O$ is triphenyl phosphine oxide.

20. The method of claim 1 wherein the infrared analyzer is online with a reactor containing the acetic acid reaction mixture.

21. The method of claim 1 wherein the infrared analyzer is offline from a reactor containing the acetic acid reaction mixture.

22. A method of manufacturing acetic acid with improved process control, comprising:
  collecting a sample of an acetic acid reaction mixture containing at least methyl iodide, water, methyl acetate and an active catalyst species of a catalyst selected from the group consisting of rhodium and iridium;
  measuring at least the concentrations of methyl iodide, water, and the active catalyst species in an infrared analyzer;
  adjusting the concentration of at least methyl iodide, water and the active catalyst species in the acetic acid reaction mixture in response to the measured concentrations of methyl iodide, water, methyl acetate and active catalyst species; and
  manufacturing acetic acid thereby.

23. The method of claim 22 wherein the infrared analyzer is a Fourier Transform infrared spectrometer.

24. The method of claim 22 further comprising measuring the concentration of methyl iodide in an infrared cell operating in a range selected from the group consisting of a mid-infrared region, an extended mid-infrared region, and combinations thereof.

25. The method of claim 22 further comprising measuring the concentration of water in an infrared cell operating in a range selected from the group consisting of a mid-infrared region, an extended mid-infrared region, and combinations thereof.

26. The method of claim 22 further comprising measuring the concentration of active catalyst species in an infrared cell operating in a mid-infrared region.

27. The method of claim 26 wherein the active catalyst species is of a rhodium catalyst.

28. The method of claim 22 wherein adjusting the concentration of at least methyl iodide, water and the active catalyst species in the acetic acid reaction mixture produces a substantially constant concentration for each of methyl iodide, water, and active catalyst species during the manufacture of acetic acid.

29. The method of claim 28 wherein the active catalyst species is of a rhodium catalyst.

30. The method of claim 22 wherein the frequency of measuring the concentration of methyl iodide, water, and the active catalyst species is at least about 30 times per hour.

31. The method of claim 22 further comprising controlling the sample temperature in a range between about 20° C. and about 130° C.

32. The method of claim 22 wherein the infrared analyzer contains a first cell operating in a mid-infrared region and a second cell operating in an extended mid-infrared region.

33. The method of claim 34 wherein the infrared analyzer utilizes a single polychromatic light source.

34. The method of claim 22 further comprising transmitting the measured concentrations to a control unit.

35. The method of claim 22 wherein the acetic acid reaction mixture contains a Group 15 oxide of the formula $R_3M=O$, wherein M is an element from Group 15 of Periodic Table and each R is independently a substituted or unsubstituted alkyl, aryl, aralkyl or alkaryl group.

36. The method of claim 35 further comprising measuring the concentration of the Group 15 oxide in the infrared analyzer.

37. The method of claim 36 further comprising measuring the concentration of Group 15 oxide in an infrared cell operating in a range selected from the group consisting of a mid-infrared region, an extended mid-infrared region, and combinations thereof.

38. The method of claim 36 further comprising adjusting the concentration of the Group 15 oxide.

39. The method of claim 35 wherein M is phosphorus.

40. The method of claim 39 wherein $R_3M=O$ is triphenyl phosphine oxide.

41. The method of claim 22 wherein the infrared analyzer is online with a reactor containing the acetic acid reaction mixture.

42. The method of claim 22 wherein the infrared analyzer is offline from a reactor containing the acetic acid reaction mixture.

43. A method of effecting process control in a reaction for the production of acetic acid, comprising:
  collecting a sample of acetic acid reaction mixture containing at least methyl iodide, water, methyl acetate and an active rhodium species;
  measuring the concentration of methyl iodide in an infrared cell operating in a range selected from the group consisting of the mid-infrared region, the extended mid-infrared region, and combinations thereof;

measuring the concentration of water in an infrared cell operating in a range selected from the group consisting of the mid-infrared region, the extended mid-infrared region, and combinations thereof;

measuring the concentration of methyl acetate in an infrared cell operating in a range selected from the group consisting of the mid-infrared region, the extended mid-infrared region, and combinations thereof;

measuring the concentration of active rhodium species in an infrared cell operating in a mid-infrared region; and adjusting the concentration of at least methyl iodide, water and the active catalyst species in the acetic acid reaction mixture in response to the measured concentrations of methyl iodide, water, and active rhodium species to produce a substantially constant concentration for each of methyl iodide, water, and active rhodium species during the manufacture of acetic acid.

* * * * *

UNITED STATES PATENT AND TRADEMARK OFFICE
CERTIFICATE OF CORRECTION

PATENT NO. : 6,103,934
DATED : August 15, 2000
INVENTOR(S) : Noel Hallinan et al.

It is certified that error appears in the above-identified patent and that said Letters Patent is hereby corrected as shown below:

Column 7,
Line 65, "arc well known" should be -- are well known --.

Column 13,
Line 43, "deutcro" should be -- deutero --.

Column 18,
Line 48, "measuring the at least" should be -- measuring at least --.

Column 19,
Line 63, water, methyl acetate and" should be -- water and --.

Column 20,
Line 33, "34" should be -- 32 --.

Column 21,
Lines 7-11, delete "measuring the concentration of methyl acetate in an infrared cell operating in a range selected from the group consisting of the mid-infrared region, the extended mid-infrared region, and combinations thereof;"

Signed and Sealed this

Fourteenth Day of May, 2002

*Attest:*

JAMES E. ROGAN
*Attesting Officer*     *Director of the United States Patent and Trademark Office*